(12) United States Patent
Rousseaux et al.

(10) Patent No.: US 11,261,166 B2
(45) Date of Patent: Mar. 1, 2022

(54) LIPOPHILIC MACROCYCLIC LIGANDS, COMPLEXES THEREOF, AND USES OF SAME

(71) Applicant: GUERBET, Villepinte (FR)

(72) Inventors: Olivier Rousseaux, Senlis (FR); Olivier Fougere, Mortefontaine (FR); Sarah Catoen, Livry Gargan (FR)

(73) Assignee: GUERBET, Villepinte (FR)

( * ) Notice: Subject to any disclaimer, the term of this patent is extended or adjusted under 35 U.S.C. 154(b) by 23 days.

(21) Appl. No.: 16/631,107

(22) PCT Filed: Jul. 20, 2018

(86) PCT No.: PCT/EP2018/069784
§ 371 (c)(1),
(2) Date: Jan. 14, 2020

(87) PCT Pub. No.: WO2019/016377
PCT Pub. Date: Jan. 24, 2019

(65) Prior Publication Data
US 2020/0231554 A1    Jul. 23, 2020

(30) Foreign Application Priority Data

Jul. 21, 2017 (FR) ................................ 17 56932

(51) Int. Cl.

| | | |
|---|---|---|
| *A61K 51/00* | (2006.01) | |
| *A61M 36/14* | (2006.01) | |
| *C07D 257/02* | (2006.01) | |
| *A61K 47/44* | (2017.01) | |
| *A61P 35/00* | (2006.01) | |
| *A61K 49/10* | (2006.01) | |

(52) U.S. Cl.
CPC ............ *C07D 257/02* (2013.01); *A61K 47/44* (2013.01); *A61P 35/00* (2018.01); *A61K 49/106* (2013.01)

(58) Field of Classification Search
None
See application file for complete search history.

(56) References Cited

U.S. PATENT DOCUMENTS

| | | | |
|---|---|---|---|
| 5,435,990 A * | 7/1995 | Cheng ................ | A61K 51/1045 424/1.53 |
| 6,187,285 B1 | 2/2001 | Meyer et al. | |
| 7,164,016 B2 | 1/2007 | Platzek et al. | |
| 8,540,966 B2 | 9/2013 | Aime et al. | |
| 10,232,060 B2 * | 3/2019 | Aime .................. | A61K 49/124 |
| 2007/0098643 A1 | 5/2007 | Nachman et al. | |
| 2016/0346202 A1 * | 12/2016 | Caroline ............. | A61K 31/704 |

OTHER PUBLICATIONS

Breeman et al. (Int. J. Cancer 2003, 104, 376-379).*
International Search Report for PCT/EP2018/069784, dated Sep. 3, 2018.
Written Opinion of the International Searching Authority for PCT/EP2018/069784, dated Sep. 3, 2018.
Preliminary Search Report for FR 1756932, dated Feb. 2, 2018.

* cited by examiner

*Primary Examiner* — Michael G. Hartley
*Assistant Examiner* — Melissa J Perreira
(74) *Attorney, Agent, or Firm* — B. Aaron Schulman, Esq.; Stites & Harbison, PLLC

(57) ABSTRACT

The present invention relates to novel lipophilic macrocyclic ligands, the complexes thereof, in particular radioactive complexes, and the uses of same in medical imaging and/or in therapy, in particular in interventional radiology.

16 Claims, 3 Drawing Sheets

LIPOPHILIC MACROCYCLIC LIGANDS, COMPLEXES THEREOF, AND USES OF SAME

The present invention relates to novel lipophilic macrocyclic ligands and complexes thereof, notably radioactive, and uses thereof in medical imaging and/or in therapy, notably in interventional radiology.

The need for targeted, personalized treatments in oncology is leading to the development of new therapeutic strategies based on tools for early detection combined with vectored treatments that are more specific and more effective.

Interventional radiology is a very promising direction in personalized medicine. It allows accurate diagnosis of the lesion or tumor and/or immediate treatment thereof, guided and monitored by the image, to be combined in the same sequence. It is described as minimally invasive surgery and so allows treatment in outpatient conditions, thus saving many expensive days of hospitalization for efficacy that is often comparable to conventional surgery. Interventional radiology may therefore represent an alternative or an addition to conventional surgical treatment.

Interventional radiology makes it possible to gain access to a lesion or tumor located inside the body for carrying out a diagnostic procedure (biopsy, for example) or a therapeutic procedure. Imaging by fluoroscopy, ultrasonography, scanner or MRI allows pinpointing, guiding and optimal monitoring of the medical procedure.

There is therefore a need for new molecules usable in medical imaging and/or in therapy, in particular in interventional radiology. More particularly, there is a need for ligands that make it possible to complex chemical elements, in particular metals, so as to obtain complexes usable in medical imaging and/or in therapy, in particular in interventional radiology. There is also a need for ligands that make it possible to complex chemical elements that can be formulated in a stable manner in compositions suitable for medical imaging and/or therapy.

These ligands must notably be stable and they have to complex the metals sufficiently strongly so that the latter reach their target and do not spread to other sensitive organs or tissues such as the bones, lungs and kidneys. These ligands must in particular make it possible to stabilize the radioactive elements in the desired pharmaceutical formulations, avoiding diffusion of the radioactivity throughout the body once administered.

The present invention aims to supply novel ligands that make it possible to complex chemical elements, in particular radioelements.

The present invention also aims to supply novel complexes, in particular radioactive complexes.

The present invention aims to supply ligands and/or complexes that are particularly useful in medical imaging and/or in therapy, notably in cancer treatment.

The present invention also aims to supply a stable pharmaceutical composition comprising complexes allowing medical imaging, targeting and/or treatment of cancers.

The present invention aims to supply a stable pharmaceutical composition allowing vectoring of complexes according to the invention, safely and effectively for the patient.

The present invention relates to a compound of the following general formula (I):

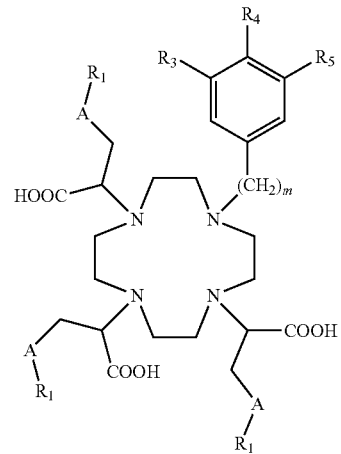

in which
$R_1$ is a methyl or a $(C_6\text{-}C_{10})$aryl;
$R_3$, $R_4$ and $R_5$ are selected independently of one another from the group consisting of: H, $(C_1\text{-}C_{20})$alkyl, $(C_2\text{-}C_{20})$alkenyl, $(C_2\text{-}C_{20})$alkynyl, $(C_6\text{-}C_{10})$aryl, $(C_1\text{-}C_{20})$alkylene-$(C_6\text{-}C_{10})$aryl, $(C_2\text{-}C_{20})$alkenylene-$(C_6\text{-}C_{10})$aryl and $(C_2\text{-}C_{20})$alkynylene-$(C_6\text{-}C_{10})$aryl;
said alkyl, alkenyl, alkynyl, alkylene, alkenylene and alkynylene groups of the radicals $R_3$, $R_4$ and $R_5$ may optionally comprise one or more $(C_6\text{-}C_{10})$arylene(s) and/or one or more $(C_5\text{-}C_{10})$cycloalkylene(s) in their chain;
and
said alkyl, alkenyl, alkynyl, aryl, alkylene, alkenylene and alkynylene groups of the radicals $R_3$, $R_4$ and $R_5$ optionally being substituted with one or more substituent(s) selected from the group consisting of:
halogen, halo$(C_1\text{-}C_{20})$alkyl, $(C_1\text{-}C_{20})$alkyl, $(C_2\text{-}C_{20})$alkenyl, $(C_2\text{-}C_{20})$alkynyl; said alkyl, alkenyl and alkynyl groups optionally comprising one or more $(C_6\text{-}C_{10})$arylene(s) in their chain;
A is a —$(CH_2)_n$— group that may optionally comprise one or more $(C_6\text{-}C_{10})$arylene(s) in its chain;
n is an integer in the range from 0 to 15, preferably from 0 to 10; and
m is an integer in the range from 1 to 10;
or a pharmaceutically acceptable salt thereof or an optical isomer thereof or a geometric isomer thereof or a tautomer thereof or a solvate thereof.

The inventors have developed novel ligand-metal complexes (complexes that are also called chelates) based on the cyclen macrocycle 1,4,7,10-tetraazacyclododecane, substituted with three identical arms on three of the nitrogen atoms, as well as with a lipophilic arm comprising at least one phenyl ring on the last nitrogen atom. The cyclen macrocycle has the following formula:

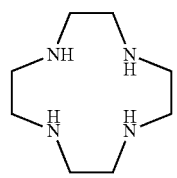 [SMILES: C1CNCCNCCNCCN1]

Surprisingly, the complexes according to the invention have good thermodynamic stability as well as good kinetic inertia. Moreover, also quite surprisingly, the inventors discovered that the complexes according to the invention could be dissolved in an iodinated oil such as LIPIODOL®, an iodinated oil manufactured and marketed by the company Guerbet and consisting of ethyl esters of iodinated fatty acids of poppyseed oil. Thus, the complexes according to the invention, dissolved in an iodinated oil such as LIPIODOL®, may be vectored notably to the liver and may make it possible to visualize and/or treat cancers, for example liver cancers.

These complexes also have a good radiochemical extraction yield in an iodinated oil such as LIPIODOL®. In particular they have good incorporation of the radioactivity in an iodinated oil such as LIPIODOL® and good stability of the radioactive solution of LIPIODOL® in in-vitro tests.

In particular, the combination of the vectoring properties of LIPIODOL®, the therapeutic efficacy of the radioelements, and the good tolerance of these products make it possible to propose therapeutic cancer treatment that is safe and easier to carry out.

Vectoring of the complexes according to the invention by an iodinated oil such as LIPIODOL® notably makes it possible to avoid poor delivery of the complexes, lowering the risk of undesirable effects in healthy organs, in particular the healthy liver or in extrahepatic organs, and makes it possible to reach the effective dose of radioactivity in the tumor.

More particularly, this vectoring makes the work of the interventional radiologist easier at the time of injection of the complexes according to the invention. For example, during an intraarterial injection monitored by fluoroscopy, the radiologist's action will be safer and more accurate, allowing adjustment of the rate of delivery of the complexes as a function of capture of the complexes according to the invention by the tumor.

Definitions

"Ligand" means a compound capable of complexing a chemical element such as a metal, preferably a radioelement. According to one embodiment, the ligands in the sense of the invention are in anionic form and are able to complex radioelements in cationic form, for example metal cations with oxidation number (III). According to the present invention, the compounds of formula (I) are ligands.

"Radioelement" means any known radioisotope of a chemical element, whether natural or produced artificially. According to one embodiment, the radioelement is selected from the radioisotopes of yttrium, rare earths and lanthanides.

"Rare earths" denotes the atoms selected from the group consisting of scandium Sc, yttrium Y, and the lanthanides.

"Lanthanides" denotes the atoms selected from the group consisting of: La, Ce, Pr, Nd, Pm, Sm, Eu, Gd, Tb, Dy, Ho, Er, Tm, Yb and Lu (i.e. lanthanum, cerium, praseodymium, neodymium, promethium, samarium, europium, gadolinium, terbium, dysprosium, holmium, erbium, thulium, ytterbium and lutetium).

"Complex" means an association of a ligand as defined above with a chemical element, preferably a radioelement as defined above. The term "complex" is a synonym of "chelate".

"Degree of extraction" or "extraction yield" means the amount of radioactivity transferred from a medium, for example a polar medium, comprising a radioactive complex according to the invention, preferably from a reaction mixture for synthesis of a radioactive complex according to the invention, to an oily phase, preferably an iodinated oil and more preferably Lipiodol®. This amount is expressed as a percentage of the radioactivity initially used, expressed in curie or in becquerel. "Reaction mixture for synthesis of a radioactive complex according to the invention" means for example a mixture of acetate buffer and ethanol.

"Radiolabeling yield" means the amount of radioactivity present in the form of a complex after the step of radiolabeling a ligand. This amount is expressed as a percentage of the radioactivity initially used expressed in curie or in becquerel.

"Thermodynamic stability" represents the affinity of the ligand for a given element, in particular a given metal. It is the equilibrium constant of the complexation reaction:

Metal+Ligand ⇌ Complex the constants of which are as follows:
Dissociation (the complex dissociating into a ligand and a metal):

$$K_D = \frac{[\text{Metal}][\text{Ligand}]}{[\text{Complex}]}$$

Association (the ligand and the metal associating to form a complex):

$$K_A = \frac{[\text{Complex}]}{[\text{Metal}][\text{Ligand}]} \text{ with } KD = \frac{1}{K_A}$$

The values are generally expressed in the form of a decimal logarithm log $K_A$ or $-\log K_D$. According to one embodiment, the complexes according to the invention have strong affinity. According to one embodiment, the complexes according to the invention have a thermodynamic equilibrium constant at least equal to 16 (Log $K_A$ at least equal to 16).

The complexes formed according to the equilibrium reaction described above are liable to dissociate under the action of various factors (pH, presence of competing metals or ligands). This dissociation may have important consequences in the context of using the complexes in human medicine as it leads to release of the metal in the body. In order to limit this risk, complexes with slow dissociation are sought, i.e. complexes having good kinetic inertia. Kinetic inertia may be determined by dissociation tests in an acid medium. These experiments lead to determination of a half-life ($T_{1/2}$) in defined conditions for each complex.

In the context of the invention, the term "treat", "treatment" or "therapeutic treatment" signifies reversing, alleviating, or inhibiting the progression of the disorder or disease to which this term is applicable, or one or more symptoms of said disorder.

The term "medical imaging" denotes the means of acquisition and reproduction of images of the human or animal body on the basis of various physical phenomena such as absorption of X-rays, nuclear magnetic resonance, reflection of ultrasonic waves or radioactivity. According to one embodiment, the term "medical imaging" refers to X-ray imaging, MRI (magnetic resonance imaging), single-photon emission tomography (SPET or SPECT for "Single Photon Emission Computed Tomography"), positron emission tomography (PET) and luminescence. Preferably, the method of medical imaging is X-ray imaging. According to a particular embodiment, the method of medical imaging is MRI if the complex according to the invention comprises Gd(III), SPECT if the complex according to the invention comprises a gamma emitter and PET if the complex according to the invention comprises a beta+emitter.

The ability of the contrast agents to accelerate the relaxation rates 1/T1 and 1/T2 of the protons of water is measured by a quantity called relaxivity. Notably the relaxivity (r) of a contrast agent is defined as the relaxation rate, normalized by the concentration of the contrast agent.

The term "$(C_1-C_{20})$alkyl" denotes saturated aliphatic hydrocarbons, which may be linear or branched and comprise from 1 to 20 carbon atoms. Preferably, the alkyls comprise from 1 to 10 carbon atoms, or even from 1 to 5 carbon atoms. "Branched" means that an alkyl group is substituted on the alkyl main chain.

The term "$(C_1-C_{20})$alkylene" denotes an alkyl radical as defined above, divalent.

The term "$(C_2-C_{20})$alkene" denotes an alkyl as defined above, comprising at least one carbon-carbon double bond.

The term "$(C_2-C_{20})$alkenylene" denotes an alkyl as defined above, comprising at least one carbon-carbon double bond and divalent.

The term "$(C_2-C_{20})$alkyne" denotes an alkyl as defined above, comprising at least one carbon-carbon triple bond.

The term "$(C_2-C_{20})$alkynylene" denotes an alkyl as defined above, comprising at least one carbon-carbon triple bond and divalent.

The term "$(C_6-C_{10})$aryl" denotes monocyclic, bicyclic or tricyclic hydrocarbon-containing aromatic compounds, in particular phenyl and naphthyl.

The term "arylene" denotes an aryl as defined above, divalent, in particular phenylene and naphthylene.

The term "$(C_5-C_{10})$cycloalkylene" denotes a cycloalkyl comprising from 5 to 10 carbon atoms, monocyclic or bicyclic, divalent. Among the cycloalkylenes, we may mention cyclopentylene or cyclohexylene.

According to one embodiment, "halogen" denotes F, Cl, Br, I, At and isotopes thereof, preferably F, Cl, Br, I and isotopes thereof. According to a particular embodiment, the halogen is a fluorine atom.

Iodinated Oils

The term "fatty acid" is understood to denote saturated or unsaturated aliphatic carboxylic acids having a carbon chain of at least 4 carbon atoms. The natural fatty acids have a carbon chain of 4 to 28 carbon atoms (generally an even number). We talk of "long-chain fatty acid" for a length of 14 to 22 carbons and "very long-chain" if there are more than 22 carbons. On the contrary, we talk of "short-chain fatty acid" for a length of 4 to 10 carbons, notably 6 to 10 carbon atoms, in particular 8 or 10 carbon atoms. A person skilled in the art knows the associated nomenclature and in particular uses:

Ci-Cp to denote a range of Ci to Cp fatty acids $C_i$+Cp, the total of the Ci fatty acids and Cp fatty acids For example:
the fatty acids with 14 to 18 carbon atoms are written "C14-C18 fatty acids"
the total of the C16 fatty acids and C18 fatty acids is written C16+C18.
for a saturated fatty acid, a person skilled in the art will use the following nomenclature Ci:0, where i is the number of carbon atoms of the fatty acid. Palmitic acid, for example, will be denoted by the nomenclature (C16:0).
for an unsaturated fatty acid, a person skilled in the art will use the following nomenclature Ci: x n-N where N will be the position of the double bond in the unsaturated fatty acid starting from the carbon opposite the acid group, i is the number of carbon atoms of the fatty acid, x is the number of double bonds (unsaturations) of this fatty acid. Oleic acid, for example, will be denoted by the nomenclature (C18:1 n-9).

Advantageously, the iodinated oil according to the invention comprises or consists of iodinated derivatives of fatty acids, preferably iodinated ethyl esters of fatty acids, more preferably of iodinated ethyl esters of fatty acids of poppyseed oil, olive oil, colza seed oil, peanut oil, soybean oil or walnut oil, even more preferably iodinated ethyl esters of fatty acids of poppyseed oil or of olive oil. More preferably, the iodinated oil according to the invention comprises or consists of iodinated ethyl esters of fatty acids of poppyseed oil (also called black poppy or *Papaver somniferum* var. *nigrum*). Poppyseed oil, also called poppy seed oil or poppy oil, preferably contains more than 80% of unsaturated fatty acids (in particular linoleic acid (C18:2 n-6) and oleic acid (C18:1 n-9)), of which at least 70% of linoleic acid and at least 10% of oleic acid. The iodinated oil is obtained from complete iodination of an oil such as poppyseed oil in conditions allowing one bond of an iodine atom for each double bond of the unsaturated fatty acids (Wolff et al. 2001, Medicine 80, 20-36) followed by a transesterification.

The iodinated oil according to the invention preferably contains from 29 to 53% (w/w), more preferably 37% to 39% (w/w) of iodine.

The following may be cited as examples of iodinated oils: Lipiodol®, Brassiodol® (derived from colza seed oil (*Brassica compestis*), Yodiol® (derived from peanut oil), Oriodol® (derived from poppyseed oil but in the form of fatty acid triglycerides), Duroliopaque® (derived from olive oil).

Preferably, the iodinated oil is Lipiodol®, an iodinated oil used as a contrast product and in certain procedures of interventional radiology. This oil is a mixture of iodinated and noniodinated ethyl esters of fatty acids of poppyseed oil. It consists predominantly (in particular, more than 84%) of a mixture of iodinated ethyl esters of long-chain fatty acids (in particular C18 fatty acids) derived from poppyseed oil, preferably a mixture of ethyl monoiodostearate and ethyl diiodostearate. The iodinated oil may also be an oil based on monoiodinated ethyl ester of stearic acid (C18:0) derived from olive oil. A product of this type, called Duroliopaque®, was put on the market some years ago.

The term "LIPIODOL" refers to an iodinated oil and preferably to the pharmaceutical specialty LIPIODOL®, injectable solution manufactured and marketed by Guerbet and consisting of ethyl esters of iodinated fatty acids from poppyseed oil. LIPIODOL® is a product notably used for visualization, localization and/or vectoring during transcatheter arterial chemoembolization of hepatocellular carcinoma at the intermediate stage, in adults, as well as for diagnosis by the selective hepatic arterial route of the hepatic extension of malignant lesions, whether or not hepatic.

The main characteristics of Lipiodol® are as follows:

| Compounds | Proportions in the fatty acid mixture |
|---|---|
| Ethyl palmitate (Ethyl C16:0) | 4.6 to 6.7% (w/w), preferably 4.8% (w/w) |
| Ethyl stearate (Ethyl C18:0) | 0.8 to 1.9% (w/w), preferably 1.2% (w/w) |
| Ethyl monoiodostearate | 11.3 to 15.3% (w/w), preferably 13.4% (w/w) |

-continued

| Compounds | Proportions in the fatty acid mixture |
|---|---|
| Ethyl diiodostearate | 73.5 to 82.8% (w/w), preferably 78.5% (w/w) |

| Other characteristics of Lipiodol ®: | |
|---|---|
| Iodine | 37% to 39% (w/w) (i.e. 480 mg/ml) |
| Viscosity | |
| at 37° C. | 25 mPa.s |
| at 20° C. | 50 mPa.s |
| Density | 1.268-1.290 g/cm$^3$ at 20° C., preferably 1.28 |

Compounds of General Formula (I)

The compounds of general formula (I) may have chiral centers and may be in racemic or enantiomeric form. The compounds of general formula (I) are comprised in their various isomeric forms including enantiomers, diastereoisomers or racemic mixtures of the pairs of enantiomers or mixtures of diastereoisomers.

The embodiments presented hereunder may be considered independently of one another or combined with one another.

According to one embodiment, the compounds of general formula (I) are in the form of salt, preferably in the form of pharmaceutically acceptable salt.

"Pharmaceutically acceptable salt" notably denotes salts allowing the properties and the biological efficacy of the compounds according to the invention to be preserved. Examples of pharmaceutically acceptable salts are given in Berge, et al. ((1977) J. Pharm. Sd, Vol. 66, 1). For example, the compounds of general formula (I) are in the form of sodium salt or meglumine (1-deoxy-1-(methylamino)-D-glucitol or N-methyl-D-glucamine).

The invention also relates to the optical isomers (enantiomers), geometric isomers (cis/trans or Z/E), the tautomers and the solvates such as the hydrates of the compounds of formula (I).

According to one embodiment, when $R_1$ is a methyl, n is an integer in the range from 4 to 8. According to one embodiment, when $R_1$ is a methyl, n is an integer in the range from 4 to 8 and when $R_1$ is a ($C_6$-$C_{10}$)aryl, n is an integer in the range from 0 to 6, preferably from 0 to 5. According to a particular embodiment, when $R_1$ is a methyl, n is an integer equal to 4, 6 or 8.

According to one embodiment, n is an integer in the range from 1 to 15, preferably from 1 to 10, more preferably from 4 to 8, for example equal to 4, 6 or 8. According to one embodiment, m is an integer in the range from 1 to 5, preferably from 1 to 3, for example equal to 1.

According to one embodiment, $R_1$ is a methyl or a phenyl. According to one embodiment, the group A and/or the radicals $R_3$, $R_4$ and/or $R_5$ comprise at most 3 arylene groups in their chain(s).

According to one embodiment, A is a group —$(CH_2)_n$—.

According to a particular embodiment, ($C_6$-$C_{10}$)aryl is a phenyl. According to one embodiment, $R_3$, $R_4$ and $R_5$ are selected independently of one another from the group consisting of: H, ($C_1$-$C_{20}$)alkyl, ($C_2$-$C_{20}$)alkenyl, ($C_2$-$C_{20}$)alkynyl, ($C_6$-$C_{10}$)aryl, ($C_1$-$C_{20}$)alkylene-($C_6$-$C_{10}$)aryl, ($C_2$-$C_{20}$)alkenylene-($C_6$-$C_{10}$)aryl and ($C_2$-$C_{20}$)alkynylene-($C_6$-$C_{10}$)aryl;

said alkyl, alkenyl, alkynyl, alkylene, alkenylene and alkynylene groups of the radicals $R_3$, $R_4$ and $R_5$ may optionally comprise one or more ($C_6$-$C_{10}$)arylene(s) in their chain; said alkyl and/or aryl groups optionally being substituted with one or more substituent(s) selected from halogens, ($C_1$-$C_{20}$)alkyls or halo($C_1$-$C_{20}$)alkyls.

According to one embodiment, $R_3$ and $R_5$ are selected independently of one another from H or ($C_1$-$C_{20}$)alkyl, said alkyl group optionally being substituted with one or more substituent(s) selected from the halogens, preferably fluorine.

Preferably, $R_3$ and $R_5$ are selected independently of one another from H, tert-butyl or $CF_3$. According to one embodiment, $R_3$ and $R_5$ are identical, preferably they are H or a tert-butyl, more preferably H.

According to one embodiment, $R_4$ is selected from the group consisting of: H, ($C_1$-$C_{10}$)alkyl, ($C_6$-$C_{10}$)aryl, ($C_1$-$C_{10}$)alkylene-($C_6$-$C_{10}$)aryl and ($C_2$-$C_{10}$)alkenylene-($C_6$-$C_{10}$)aryl and ($C_2$-$C_{10}$)alkynylene-($C_6$-$C_{10}$)aryl;

said alkyl, aryl, alkylene and alkenylene groups optionally being substituted with one or more substituent(s) selected from the halogens or the halo($C_1$-$C_{20}$)alkyls.

According to one embodiment, $R_3$, $R_4$ and $R_5$ are selected from the group consisting of: H, ($C_1$-$C_{20}$)alkyl, ($C_6$-$C_{10}$)aryl and ($C_1$-$C_{20}$)alkylene-($C_6$-$C_{10}$)aryl;

said alkyl, aryl and alkylene groups of the radicals $R_3$, $R_4$ and $R_5$ optionally being substituted with one or more $CF_3$ groups.

According to one embodiment, $R_4$ is selected from the group consisting of: H, ($C_1$-$C_{20}$)alkyl, phenyl and ($C_1$-$C_{20}$)alkylene-phenyl. According to another embodiment, $R_4$ is selected from the group consisting of: H, tert-butyl, phenyl, —$CH_2$—$CH_2$-phenyl, and —$(CH_2)_7$—$CH_3$.

According to one embodiment, the compounds according to the invention are of the following general formula (I-1):

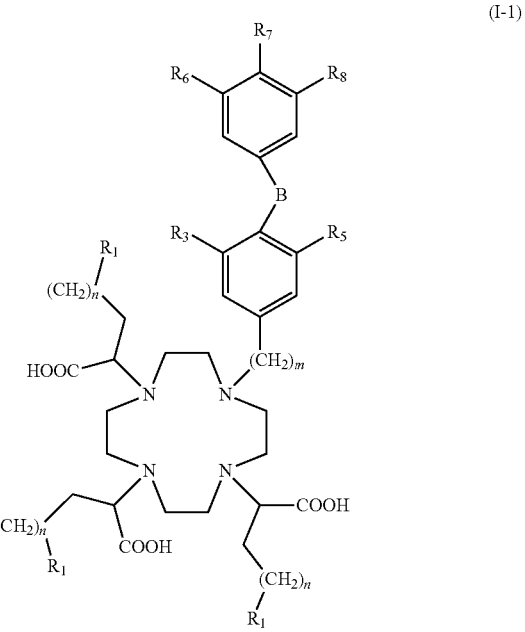

(I-1)

in which:

$R_1$, $R_3$, $R_5$, n and m are as defined in claim 1, with n preferably being equal to 6 or equal to 8;

B is a bond, a $(C_1-C_{20})$alkylene, a $(C_2-C_{20})$alkenylene or a $(C_2-C_{20})$alkynylene; and $R_6$, $R_7$ and $R_8$ are selected, independently of one another, from H and $(C_1-C_{20})$alkyl. Preferably, $R_6$ and $R_8$ are H and $R_7$ is $(C_1-C_{20})$alkyl.

According to a particular embodiment, the compounds according to the invention are of the following general formula (I-1-1):

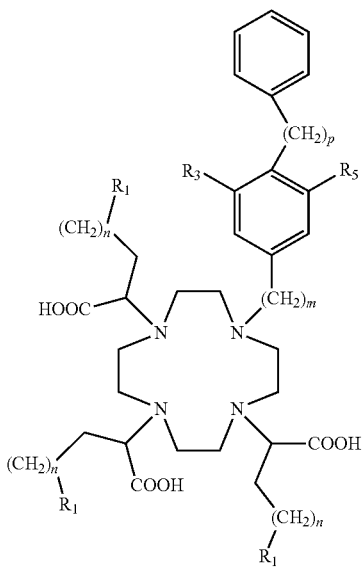

(I-1-1)

in which $R_1$, $R_3$, $R_5$, n and m are as defined above, with n preferably being equal to 6, and p is an integer in the range from 0 to 10, preferably from 0 to 5, for example equal to 0, 1, 2 or 3.

According to one embodiment, the compounds according to the invention are of the following general formula (I-2):

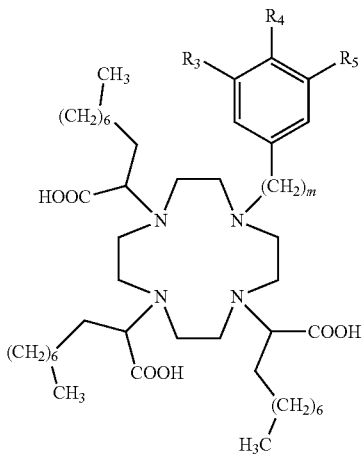

(I-2)

in which $R_3$, $R_4$, $R_5$ and m are as defined above.

According to one embodiment, the compounds according to the invention are of the following general formula (I-3):

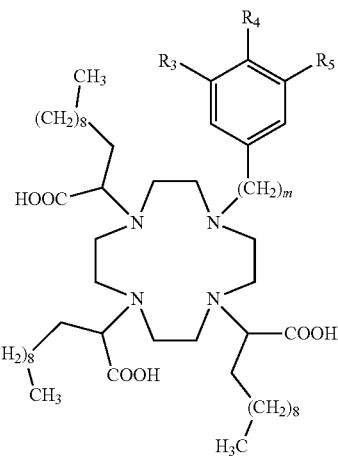

(I-3)

in which $R_3$, $R_4$, $R_5$ and m are as defined above.

According to one embodiment, the compounds according to the invention are of the following general formula (I-4):

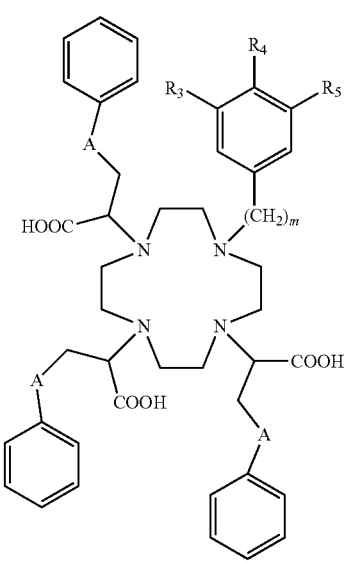

(I-4)

in which $R_3$, $R_4$, $R_5$, A and m are as defined above.

The present invention also relates to a compound selected from the group consisting of the following compounds:

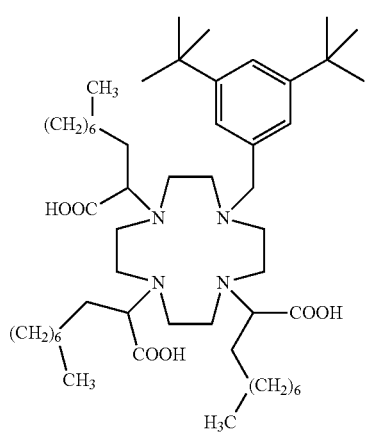

G3

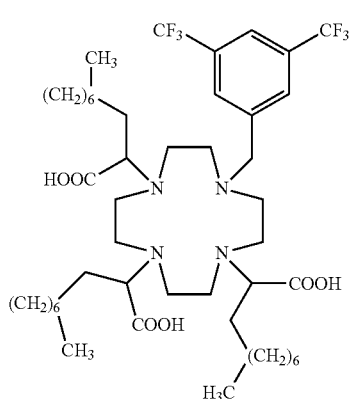
G4
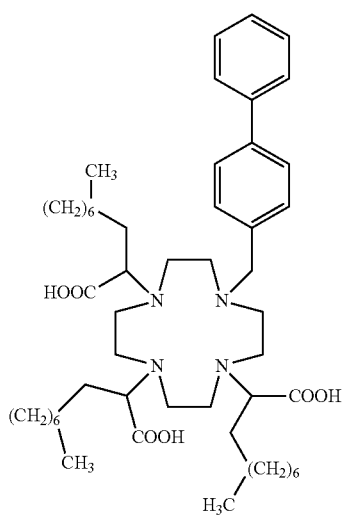
G6
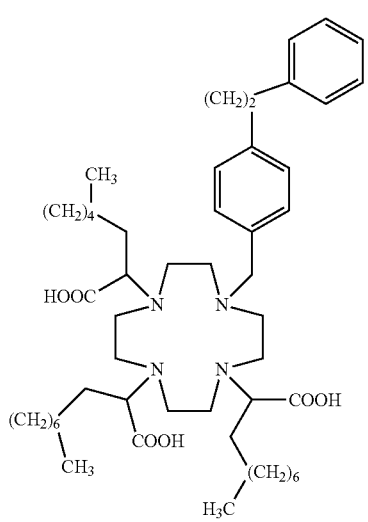
G5
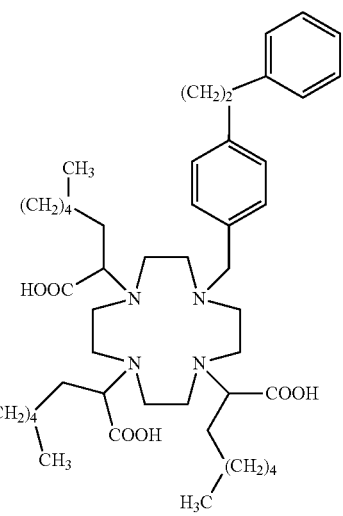
G9
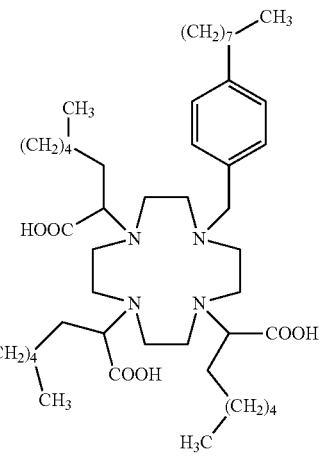
G8
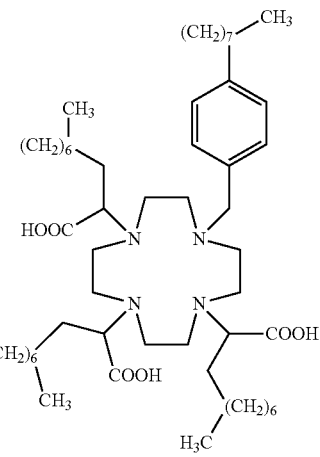
G7

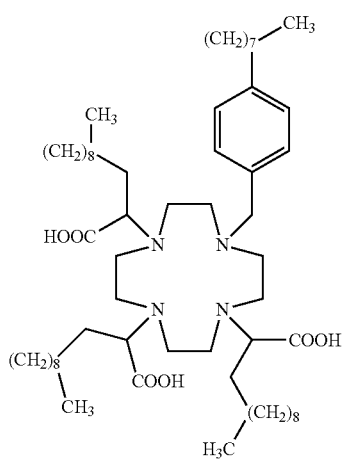
G2
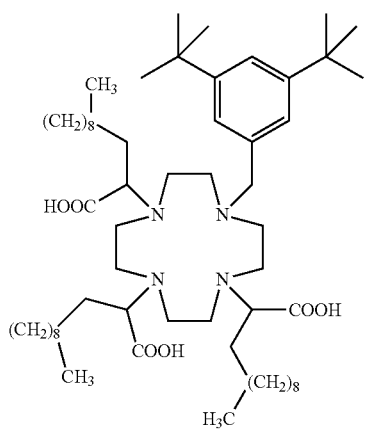
G1
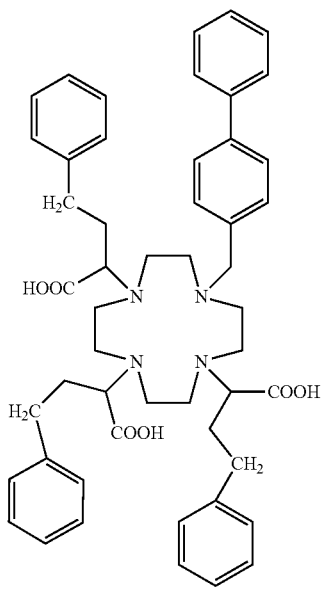
G10
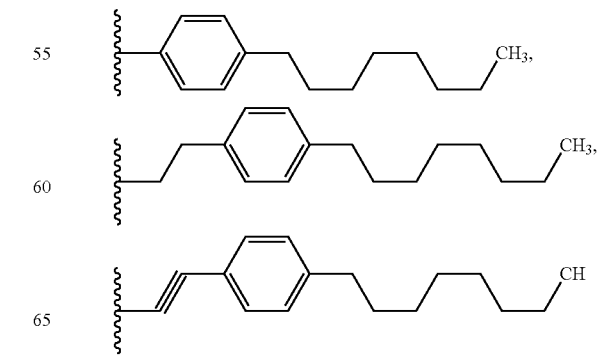
G11
G12
or their pharmaceutically acceptable salts.
According to one embodiment, the radicals $R_3$, $R_4$ and $R_5$, preferably $R_4$ are selected from:
H, tert-butyl, phenyl, —CH₂—CH₂-phenyl, —(CH₂)₇—CH₃,

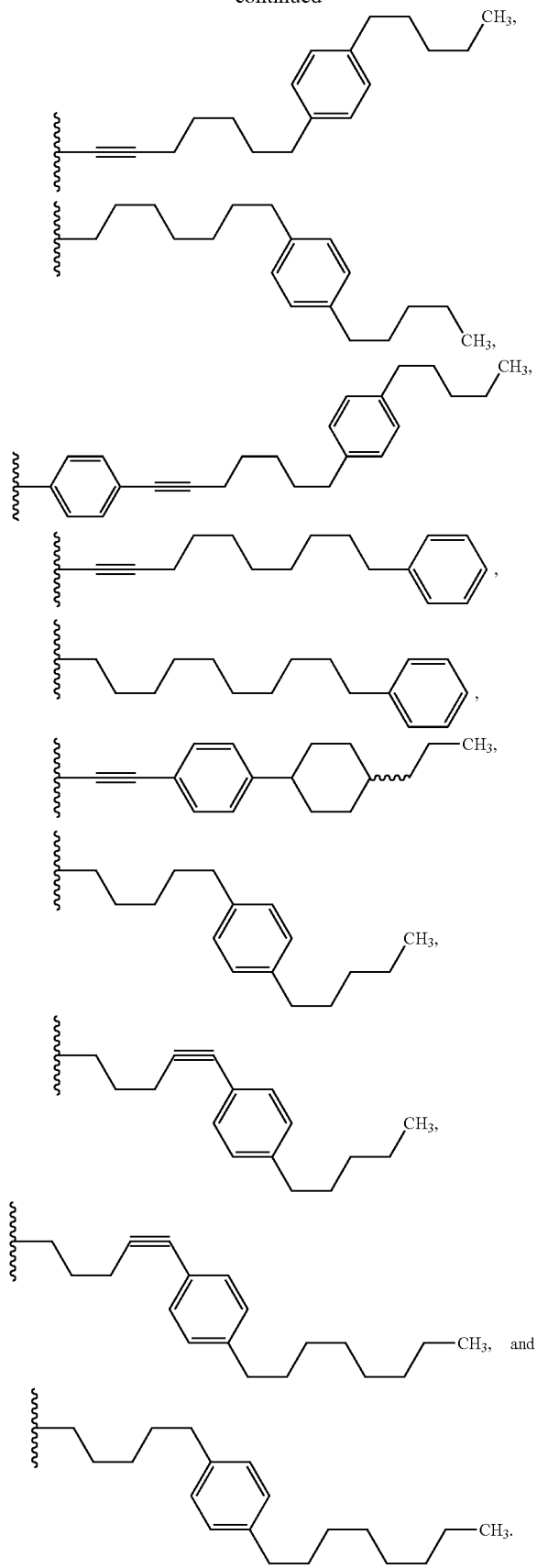

Complexes

The invention also relates to a complex of a compound of formula (I) or of a salt thereof, as defined above, with a chemical element M, preferably a metal. Preferably, M is a radioelement.

According to one embodiment, the chemical element M is a metal cation selected from the group consisting of bismuth (III), lead(II), copper(II), copper(I), gallium(III), zirconium (IV), technetium(III), indium(III), rhenium(VI), astatine (III), samarium(III), actinium(III), lutetium(III), terbium (III), holmium(III), gadolinium(III), europium(III) and yttrium(III), preferably yttrium(III).

According to a particular embodiment, the chemical element M is a radioelement selected from the group consisting of $^{212}Bi(^{212}Pb)$, $^{213}Bi(III)$, $^{64}Cu(II)$, $^{67}Cu(II)$, $^{68}Ga(III)$, $^{89}Zr(IV)$, $^{99}mTc(III)$, $^{111}In(III)$, $^{186}Re(VI)$, $^{188}Re(VI)$, $^{211}At$ (III), $^{225}Ac(III)$, $^{153}Sm(III)$, $^{149}Tb(III)$, $^{166}Ho(III)$, $^{212}Pb(II)$, $^{177}Lu(III)$ and $^{90}Y(III)$, preferably $^{212}Bi(^{212}Pb)$, $^{213}Bi(III)$, $^{64}Cu(II)$, $^{67}Cu(II)$, $^{68}Ga(III)$, $^{89}Zr(IV)$, $^{99}mTc(III)$, $^{111}In(III)$, $^{186}Re(VI)$, $^{188}Re(VI)$, $^{211}At(III)$, $^{225}Ac(III)$, $^{153}Sm(III)$, $^{149}Tb(III)$ and $^{166}Ho(III)$, and even more preferably $^{177}Lu(III)$, $^{90}Y(III)$ and $^{166}Ho(III)$.

According to one embodiment, the chemical element M is selected from Sc, Y, the lanthanides or a radioactive isotope thereof. Preferably, M is a radioelement selected from the radioactive isotopes of yttrium and of the lanthanides. According to one embodiment, M is selected from the lanthanides, the rare earths or yttrium, or a radioactive isotope thereof.

According to one embodiment, M is selected from: Sc, Y, La, Ce, Pr, Nd, Pm, Sm, Eu, Gd, Tb, Dy, Ho, Er, Tm, Yb and Lu.

According to one embodiment, M is selected from the following radioactive isotopes: $^{48}Sc$, $^{86}Y$, $^{90}Y$, $^{140}La$, $^{143}Ce$, $^{153}Sm$, $^{149}Tb$, $^{152}Tb$, $^{155}Tb$, $^{161}Tb$, $^{166}Ho$ and $^{177}Lu$.

In particular, among the radioelements according to the invention, we may mention: $^{166}Ho$, $^{177}Lu$, $^{149}Tb$, $^{152}Tb$, $^{155}Tb$, $^{161}Tb$, $^{86}Y$, $^{90}Y$ and $^{153}Sm$. According to a particular embodiment, M is a radioelement selected from the group consisting of $^{166}Ho$, $^{177}Lu$ and $^{90}Y$.

According to one embodiment, said complex is of the following general formula (III):

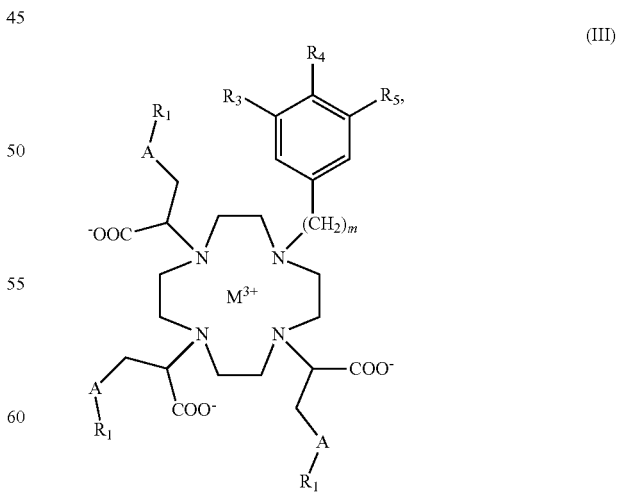

(III)

in which $R_1$, $R_3$, $R_4$, $R_5$, A, m and M are as defined above. In particular, in the general formula (III), the groups COO⁻ allow complexation to the element M.

According to one embodiment, the radiolabeling yield of the ligands according to the invention is between 10 and 100%, preferably between 75% and 99%.

Method for Preparing the Compounds of General Formula (I)

The invention also relates to a method for preparing the compounds of general formula (I), comprising the following steps:

a) a step of alkylation of the cyclen-glyoxal of the following formula (A):

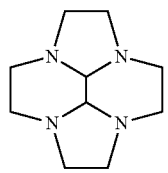

(A)

by an alkylating agent of the following formula (B1):

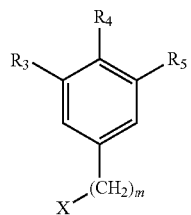

(B1)

with $R_3$, $R_4$, $R_5$ and m being as defined above and X being a halogen or a leaving group selected from mesyl ($CH_3$—$SO_2$—O—), tosyl ($CH_3$—PH—$SO_2$—O—) and triflyl ($CF_3$—$SO_2$—O—);

to obtain a compound of formula (IC):

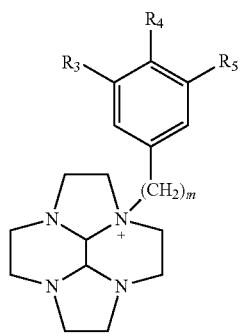

(IC)

in which $R_3$, $R_4$, $R_5$ and m are as defined above;

b) a step of deprotection of the compound of formula (IC) to obtain a compound of the following formula (ID):

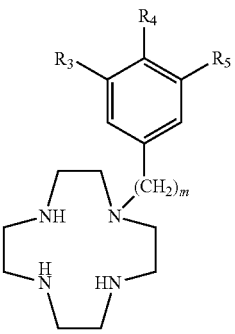

(ID)

in which $R_3$, $R_4$, $R_5$ and m are as defined above;

c) a step of alkylation of the compound of formula (ID) by an alkylating agent selected from the compounds of the following formula (B2):

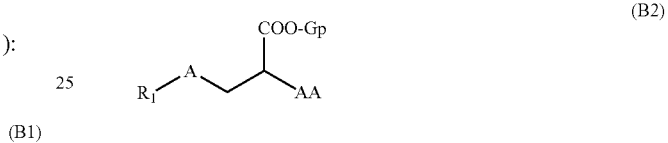

(B2)

with AA being selected from the halogen atoms, mesyl ($CH_3$—$SO_2$—O—) and triflyl ($CF_3$—$SO_2$—O—) and in which $R_1$ and A are as defined above and Gp is a protective group of the carboxylic acid function, for example a ($C_1$-$C_5$)alkyl, preferably an ethyl; to obtain a compound of the following formula (IF):

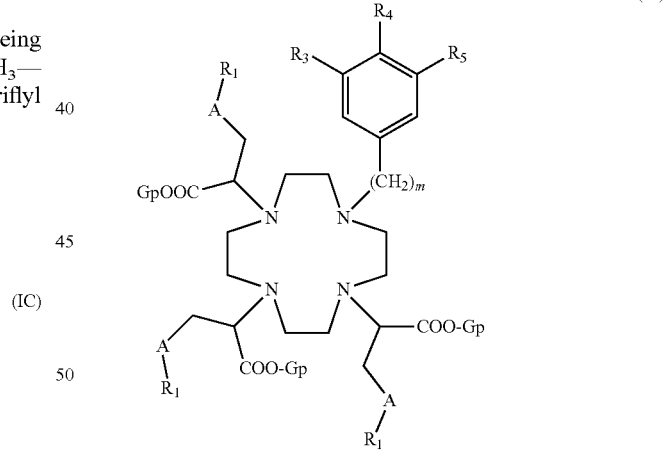

(IF)

in which Gp, A, $R_1$, $R_3$, $R_4$, $R_5$ and m are as defined above;

d) a saponification step to obtain a compound of formula (I) as defined above.

According to one embodiment, step a) is carried out in the presence of toluene, at a temperature between 50° C. and 70° C., for example about 60° C. According to one embodiment, step b) is carried out in the presence of aqueous potash or hydrazine monohydrate. According to one embodiment, step c) is carried out in the presence of anhydrous acetonitrile and $K_2CO_3$. According to one embodiment, step d) is carried out in the presence of KOH and ethanol. Preferably, steps a), b) and c) are carried out under argon.

Pharmaceutical Composition

The invention also relates to a pharmaceutical composition comprising a compound of formula (I) as defined above or a complex as defined above, and optionally one or more pharmaceutically acceptable excipients.

The composition may further comprise a buffer selected from the buffers of established usage for example such as the buffers lactate, tartrate, malate, maleate, succinate, ascorbate, carbonate, Tris((hydroxymethyl)aminomethane), HEPES (2-[4-(2-hydroxyethyl)-1-piperazine]ethanesulfonic acid), MES (2-morpholino-ethanesulfonic acid) and mixtures thereof.

The pharmaceutical composition may comprise an oily phase, notably an iodinated oil as defined above. According to a particular embodiment, the pharmaceutical composition further comprises iodinated ethyl esters of fatty acids of poppyseed oil.

According to one embodiment, the pharmaceutical composition according to the invention consists of an iodinated oil and of complexes according to the invention. Typically, the pharmaceutical composition according to the invention consists of LIPIODOL® and of complexes according to the invention. LIPIODOL® consists of iodinated ethyl esters of fatty acids of poppyseed oil.

According to one embodiment, the degree of extraction of the complexes according to the invention in an oily phase as defined above is between 35% and 100%, preferably between 75% and 100%.

The complexes according to the invention are notably extractable in an oily phase. They also make it possible to obtain compositions comprising a stable oily phase: in the presence of an aqueous medium, such as normal saline solution, the loss of the complexes according to the invention in the aqueous medium is slight, for example between 0% and 20%, for up to at least 15 days.

Preferably, the pharmaceutical composition according to the invention is radiopaque, and therefore visible by X-raying.

According to a particular embodiment, the pharmaceutical composition is an injectable composition. According to one embodiment, the pharmaceutical composition according to the invention is administered by intraarterial hepatic injection.

The invention relates to a complex or a pharmaceutical composition as defined above, for use in cancer treatment.

The invention also relates to a complex or a pharmaceutical composition as defined above, for use in medical imaging.

The invention relates to the use of a complex as defined above for preparing a drug for treating cancers.

The invention also relates to the use of a complex or of a pharmaceutical composition as defined above in medical imaging.

The invention relates to a method for therapeutic treatment of a cancer patient, comprising administration of a complex or of a pharmaceutical composition as defined above to said patient. In particular, said method of treatment does not comprise a step of surgical treatment.

The invention also relates to a method of medical imaging of a tumor comprising:
- a step of administration of a complex or of a pharmaceutical composition according to the invention to a cancer patient; and
- a step of detecting the tumor by a method of medical imaging.

"Cancer" means an abnormal cellular proliferation (also called tumor) within a normal tissue of the body. These cancer cells all derive from one and the same clone, the cancer initiating cell, which has acquired certain characteristics allowing it to divide indefinitely. In the course of development of the tumor, certain cancer cells may migrate out of their site of production and form metastases.

Among cancers, we may notably mention liver cancers, in particular primary liver cancers, preferably hepatocarcinomas. According to a particular embodiment, among the cancers we may mention hepatocarcinoma, epithelioid hemangioendothelioma, cholangiocarcinoma, neuroendocrine tumors and the metastases of other cancers such as metastases of colorectal cancer.

According to a particular embodiment, the cancer is a hepatocellular carcinoma at the intermediate stage, in an adult.

EXAMPLES

Figure 1:
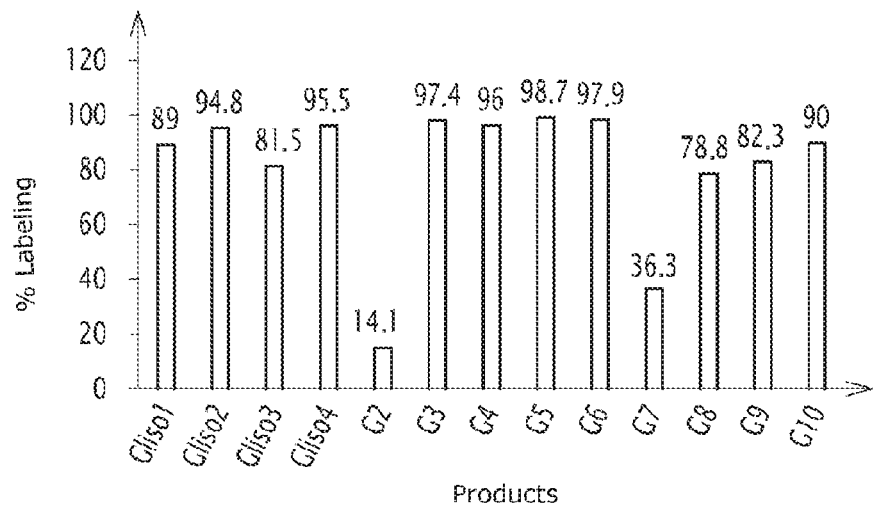
FIG. 1 shows the radiolabeling yield as a percentage for ligands according to the invention.

I. General Experimental Conditions:

The commercial products as well as the solvents used for these syntheses are obtained essentially from the companies Sigma-Aldrich®, Merck®, Interchim® and VWR®.

The ambient temperature of the room generally varies between 20° C. and 25° C. Solvent evaporation is carried out at reduced pressure, using a Buchi R-210 evaporator, at temperatures of about 40° C. The reactions and purifications are monitored by thin-layer chromatography (TLC) using silica glass plates (silica gel 60 F254), developed under UV and with iodine. The purifications are carried out on flash chromatography apparatus GRACE Reveleris® or CombiFlash® Rf obtained from Teledyne Isco®. The cartridges used for the purifications on silica are essentially GRACE Reveleris® cartridges (40 μm, 4 or 12 g). The microwave-activated reactions were carried out in the Monowave Series Anton Paar® reactor.

The purifications by preparative HPLC are carried out on PuriFlash® 4250 with Symmetry column (150×30 mm; 5 μm).

The HPLC chromatograms are recorded on an Agilent Technologies® instrument of series 1200. Detection is generally performed at 201 nm and 270 nm. In certain cases, a Corona or ELSD detector is required. The columns used are obtained from various suppliers: Waters® (Symmetry C18), Phenomenex® (Luna C8) and ACE® (C4 ACE). The mass spectrometry analyses were performed by liquid chromatography coupled to an amaZon X mass spectrometer from Bruker®.

II. Synthesis of the Ligands:

Note: in the following examples, the term "Ar" denotes a phenyl substituted with the radicals $R_3$, $R_4$ and $R_5$ such as according to the invention.

Example 1: Preparation of Alkylating Agents

1—General Procedure for Transformation of the Alcohol Derivatives

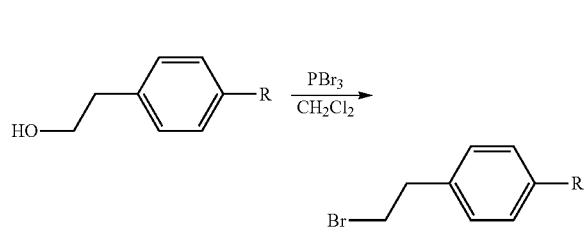

Bromination:

The alcohol derivative is diluted in dichloromethane, and then PBr$_3$ (dissolved in dichloromethane) is added dropwise to the solution previously cooled in an ice/acetone bath. The reaction mixture is stirred at room temperature for 2 hours and then treated with 10 mL of water. The organic phase is recovered, purified on a silica plug (Heptane/DCM (1:1)), dried over Na$_2$SO$_4$ and concentrated to dryness.

Mesylation:

A three-necked flask is charged with the alcohol (3.64 mmol, 1 equivalent) diluted in 15 mL of DCM (4 mL/mmol). The solution is cooled in a water/ice bath, and Et$_3$N (2 equiv) and mesyl chloride (1.2 equivalent) are added dropwise through a septum. The reaction mixture is stirred for 10 minutes and then 15 mL of water is added. The organic phase is recovered, dried over Na$_2$SO$_4$ and concentrated to dryness. A yellow solid is obtained, which will be purified on a silica plug with the Heptane/DCM mixture (4:6).

Example 2: Alkylation of Cyclen-Glyoxal A

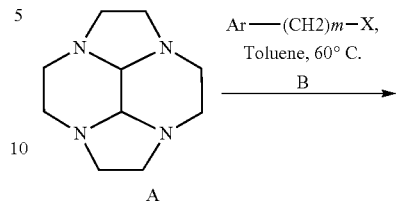

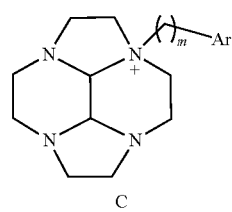

Cyclen-glyoxal A (1.2 eq, 5.6 mmol) is dissolved in 4 mL of toluene, and the alkylating agent B where X is a halogen or a mesyl (1 eq, 2.16 mmol) is added. The reaction mixture is then stirred under argon at 60° C. for 5 hours to 5 days (depending on the nature of the alkylating agent B). At the end of the reaction, the solid that has precipitated is filtered and washed abundantly with toluene. After drying in a desiccator, the product C obtained is used without further purification.

TABLE 1

| | Preparation of certain alkylating agents B | | | |
|---|---|---|---|---|
| Alkylating agent B | Expected product | Type | Yield | Molecular weight (g/mol) |
| 1-bromo-8-phenyloctane | 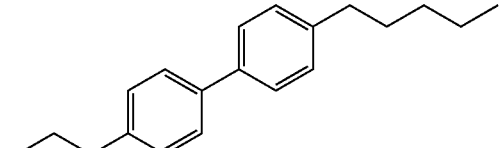 | Bromination | 31% | 331.30 |
| 4-(2-Bromoethyl)-4'-octyl-1,1'-biphenyl | 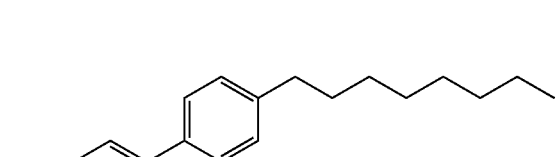 | Bromination | 33.3% | 372.15 |
| 4-(2-Bromoethyl)-4'-pentyl-1,1'-biphenyl |  | Mesylation | 43% | 352.11 |

TABLE 2 alkylation of cyclen-glyoxal A

| Alkylating agent B | Expected product C | Reaction time | Yield | M** | MS (ES+)* | HPLC (retention time tr) |
|---|---|---|---|---|---|---|
| (Bromomethyl)-1-di-tert-butyl-3,5-benzene | | 5 hours | 97% | 374.6 | $C_{23}H_{42}N_4$ 397.2 [M + Na]$^+$ | 6.16 min* |
| (Bromomethyl)-1-di(trifluoromethyl)-3,5-benzene | | 4 days | 90% | 421.2 | $C_{19}H_{23}F_6N_4Br$ 421.1 | 5.23 min* |
| Chloromethyl-1-n-octyl-4-benzene | | 18 hours | 57% | 397.3 | $C_{25}H_{41}N_4$ 397.2 | 5.4 min* |
| (Chloromethyl)-4-diphenyl-1,2-ethane | | 24 hours | 74% | 389.6 | $C_{25}H_{33}N_4$ 389.5 | 5.8 min* |
| Chloro-4-Phenylbenzyle | | 3 hours | 80% | 361.5 | $C_{23}H_{29}N_4$ 361.1 | 7.39 min* |

TABLE 2-continued alkylation of cyclen-glyoxal A

| Alkylating agent B | Expected product C | Reaction time | Yield | M** | MS (ES+)* | HPLC (retention time tr) |
|---|---|---|---|---|---|---|
| (Bromo-2-ethyl)-methyl-3-benzene | 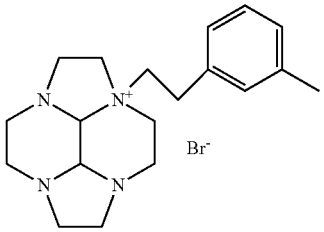 [SMILES: Cc1cccc(CC[N+]23CCN4CCN5CCN(CC2)C3C54)c1 ; [Br-]] | 48 hours | 70-90% | 313.47 | $C_{19}H_{29}N_4$ 313 | 4.77 min* |
| (Bromo-3-propyl)-benzene | 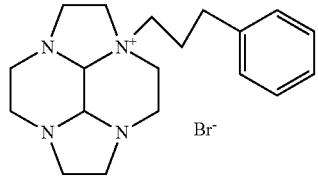 [SMILES: c1ccc(CCC[N+]23CCN4CCN5CCN(CC2)C3C54)cc1 ; [Br-]] | 48 hours | 98% | 313.47 | $C_{19}H_{29}N_4$ 313 | 4.64 min* |
| 1-bromo-8-phenyloctane | 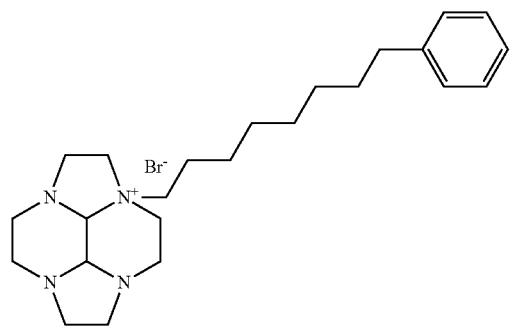 [SMILES: c1ccc(CCCCCCCC[N+]23CCN4CCN5CCN(CC2)C3C54)cc1 ; [Br-]] | 60 hours | 79% | 383.6 | $C_{24}H_{39}N_4$ 383.35 $[M + H]^+$ | 6.96 min** |
| 4-(2-Bromoethyl-4'-octyl-1,1'-biphenyl | 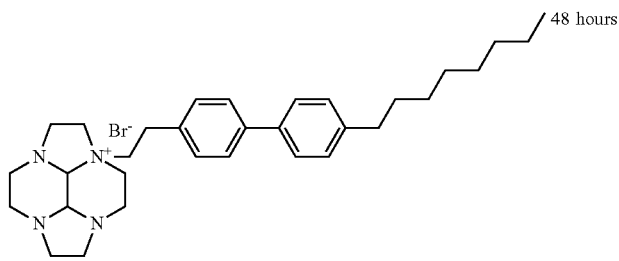 | 48 hours | 56% | 487.76 | $C_{32}H_{47}N_4$ | 9.36 min** |
| 4-(2-Bromoethyl)-4'-pentyl-1,1'-biphenyl | 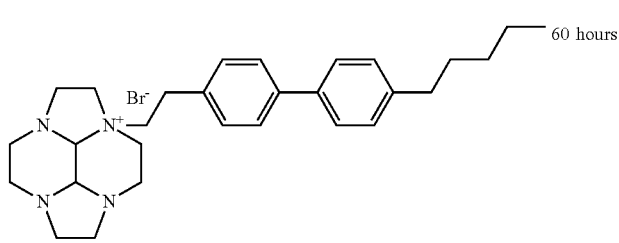 | 60 hours | 76% | 445.68 | $C_{29}H_{41}N_4$ 445.38 $[M + H]^+$ | 8.1 min** |

TABLE 2-continued alkylation of cyclen-glyoxal A

| Alkylating agent B | Expected product C | Reaction time | Yield | M** | MS (ES+)* | HPLC (retention time tr) |
|---|---|---|---|---|---|---|
| 4-(2-mesylethyl)-1,1':3',1''-terphenyl | 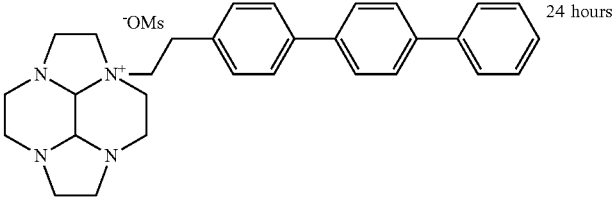 | 24 hours | 90% | 466.66 | $C_{30}H_{35}N_4$ | 10.65 min** |

*Sunfire ™ C-18 column (Waters ®), 3.5 μm, 150 × 4.6 mm, 98/2 Water (0.05% HCOOH)/CH$_3$CN in 10 min 100% CH$_3$CN
**Symmetry C-18 column, Waters, 3.5 μm, 150 × 4.6 mm; 98/2 Water (0.05% TFA)/CH$_3$CN in 12 min 100% CH$_3$CN and 8 min at 100%.
***MS (ES+) corresponds to the results of mass spectrometry with an electrospray ionization modality in positive mode.
M****: Molecular weight (g/mol)

Example 3: Deprotection of the Monoalkylated Cyclen-Glyoxal C

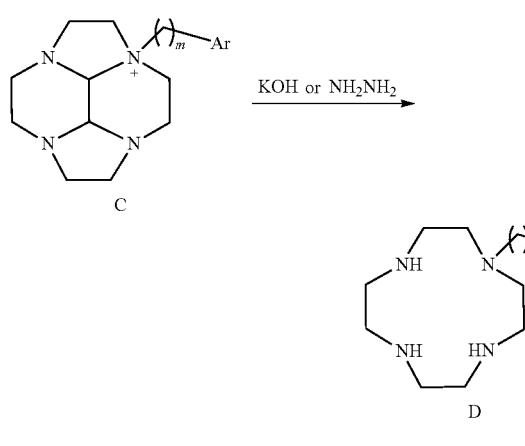

The monoalkylated cyclen-glyoxal C (1 eq, 1.5 mmol) is dissolved in aqueous potash (20%, 10 mL) or in hydrazine monohydrate (NH$_2$—NH$_2$—H$_2$O, 3 mL). The reaction mixture is then heated and stirred under argon.

With Microwave Heating:

The product is put in a glass tube with 2M potash solution and it is placed in the cavity of the Anton Paar reactor. The heating cycle is carried out, programming a temperature ramp of 10 minutes and then heating at constant temperature (180° C.) for 1 hour.

Treatment:

Reaction with Potash:

The mixture is extracted with chloroform (×3). The organic phases are combined, dried, filtered and then evaporated. The desired product D is obtained in the form of an oil or a solid. In certain cases, purification on a basic alumina column is necessary.

Reaction with Hydrazine:

The reaction mixture is cooled. The solid obtained is filtered and then taken up in ethanol. The mixture is concentrated at reduced pressure. The desired product D is obtained in the form of an oil or a solid. In certain cases, purification on a basic alumina column is necessary.

TABLE 3

Deprotection of the monoalkylated cyclen-glyoxal C

| Product D | Base | Reaction time | Yield | M**** | MS (ES+) | HPLC (retention time tr) |
|---|---|---|---|---|---|---|
| 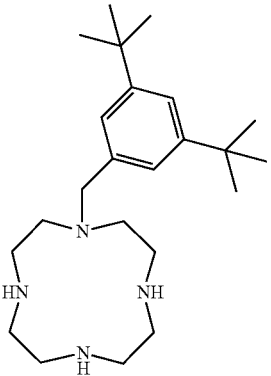 [SMILES: CC(C)(C)c1cc(CN2CCNCCNCCNCC2)cc(C(C)(C)C)c1] | Potash<br>Hydrazine | 5 days<br>4 hours | 81% | 374.6 | $C_{23}H_{42}N_4$<br>397.25<br>[M + Na]$^+$ | 3.3 min* |

TABLE 3-continued

Deprotection of the monoalkylated cyclen-glyoxal C

| Product D | Base | Reaction time | Yield | M**** | MS (ES+) | HPLC (retention time tr) |
|---|---|---|---|---|---|---|
| 3,5-bis(trifluoromethyl)benzyl-cyclen | Potash Hydrazine | 5 days 18 hours | 84% | 398.4 | $C_{17}N_{24}F_6N_4$ 421.10 $[M+H]^+$ | 1.8 min* |
| 4-heptylbenzyl-cyclen | Hydrazine | 18 hours then 2 days at 20° C. | 32% | 374.6 | $C_{23}H_{42}N_4$ 375.25 $[M+H]^+$ | 3.5 min* |
| 4-(2-phenylethyl)benzyl-cyclen | Hydrazine | 18 hours | 91% | 366.6 | $C_{23}H_{34}N_4$ 367.19 $[M+H]^+$ | 1.8 min* |
| 4-biphenylmethyl-cyclen | Potash | 6 days at 60° C. | 83% | 338.5 | $C_{21}H_{30}N_4$ 339.16 $[M+H]^+$ | 7.63 min* |
| 3-methylphenethyl-cyclen | Hydrazine | 2 hours at 100° C. | 92% | 290.46 | C17H30N4 291 $[M+H]^+$ | 4.59 min* |

TABLE 3-continued

Deprotection of the monoalkylated cyclen-glyoxal C

| Product D | Base | Reaction time | Yield | M**** | MS (ES+) | HPLC (retention time tr) |
|---|---|---|---|---|---|---|
| (cyclen with 3-phenylpropyl substituent) | Hydrazine | 2 hours at 100° C. | 90% | 290.46 | C17H30N4 291 [M + H]+ | 4.84 min* |
| (cyclen with 6-phenylhexyl substituent) | Hydrazine | 2 hours | 76% | 360.59 | C22H40N4 361.25 [M + H]+ | 7.12 min** |
| (cyclen with biphenyl-octyl substituent) | Hydrazine | 4 hours | 85% | 464.74 | C30H48N4 | 9.0 min** |
| (cyclen with biphenyl-pentyl substituent) | Hydrazine | 2 hours | 56% | 422.66 | C27H42N4 423.4 [M + H]+ | 8.03 min** |

*Sunfire ™ C-18 column (Waters ®), 3.5 μm, 150 × 4.6 mm, 98/2 Water (0.05% HCOOH)/CH3CN in 10 min 100% CH3CN
**Symmetry C-18 column, Waters, 3.5 μm, 100 × 4.6 mm 98/2 Water (0.05% TFA)/CH3CN in 12 min 100% CH3CN and 8 min at 100%
M****: Molecular weight (g/mol)

Example 4: Alkylation of the Monoalkylated Cyclen D

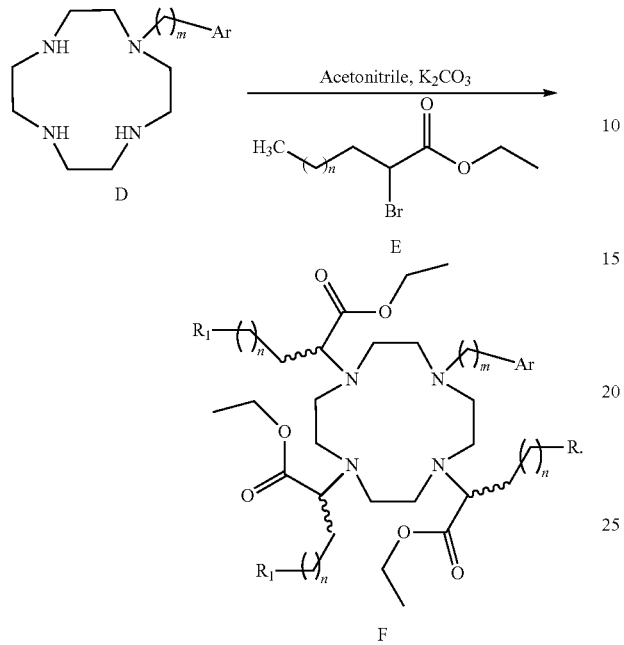

TABLE 4

| Alkylating agents E | | |
|---|---|---|
| Structures of E | Names | Empirical formulas, RN, MW (g/mol) |
| ![E1 structure] | Ethyl ester of bromo-2-dodecanoic acid racemic E1 | $C_{14}H_{27}BrO_2$, 6974-87-4, 307.27 |
| ![E2 structure] | Ethyl ester of bromo-2-decanoic acid racemic E2 | $C_{12}H_{23}BrO_2$, 6974-85-2, 279.22 |
| ![E3 structure] | Ethyl ester of bromo-2-octanoic acid racemic E3 | $C_{10}H_{19}BrO_2$ 5445-29-4 251.16 |

The monoalkylated cyclen D (1 eq, 1.5 mmol) is dissolved in anhydrous acetonitrile (5 mL), and $K_2CO_3$ (3.2 eq, 4.8 mmol) is added. The alkylating agent E (3.5 eq, 5.25 mmol), previously dissolved in acetonitrile (3 mL), is added dropwise to the mixture. The reaction mixture is then heated under reflux for 18 hours under argon. At the end of the reaction, the salts are filtered and the filtrate is evaporated. The oil obtained containing F is then purified by silica column flash chromatography: 100% of dichloromethane and then progressive addition of methanol up to proportions 80/20.

TABLE 5

Alkylation of the monoalkylated cyclen D

| Types | Codes | Substituents | Yields | Molecular weights (g/mol) | MS (ES+) | HPLC (retention time (tr) |
|---|---|---|---|---|---|---|
| C12 | F1 | -N-(3,5-di-tert-butyl)benzyle | 31% | 1053.70 | $C_{65}H_{120}N_4O_6$ | * |
|  | F2 | -N-(4-n-octyl)benzyle | 29% | 1053.70 | $C_{65}H_{120}N_4O_6$ 1053.9 $[M + H]^+$ | 10.6 min* |
| C10 | F3 | -N-(3,5-di-tert-butyl)benzyle | 46% | 969.5 | $C_{59}H_{108}N_4O_6$ 969.98 $[M + H]^+$ | 9.9 min* |
|  | F4 | -N-[3,5-Bis(trifluomethyl]benzyle | 36% | 992.7 | $C_{53}H_{90}F_6N_4O_6$ 993.71 $[M + H]^+$ | 9.9 min* |
|  | F5 | N-[4-(2-PhenylEthyl)-benzyl] | 23% | 961.48 | $C_{59}H_{100}N_4O_6$ 961.92 | 8.9 min* |
|  | F6 | -N-(4-phenyl)benzyle | 17.5% | 933.46 | $C_{67}H_{96}N_4O_6$ 933.78 | 8.5 min* |
|  | F7 | N-(4-n-octyl)benzyle | 55% | 969.54 | $C_{59}H_{108}N_4O_6$ | 9.6 min* |
|  | F11 | N-(2-(4'-pentyl-[1,1'-biphenyl]-4-yl)ethy) | 21% | 1017.58 | $C_{63}H_{108}N_4O_6$ 1017.90 $[M + H]^+$ | 10.9 min** |
|  | F12 | N-(2-(4'-octyl-[1,1'-biphenyl]-4-yl)ethyl) | 30% | 1059.66 | $C_{66}H_{114}N_4O_6$ 1017.85 $[M + H]^+$ (methyl triester)**** | 11.23 min, 11.81 min** |
| C8 | F8 | -N-(4-n-octyl)benzyle | 33% | 884.7 | $C_{52}H_{94}N_4O_6$ 885.85 $[M + H]^+$ | 8.5 min* |
|  | F9 | -N-[4-(2-PhenylEthyl)-benzyl] | 56% | 877.3 | $C_{53}H_{88}N_4O_6$ 877.82 $[M + H]^+$ | 8.0 min* |

*Sunfire ™ C-18 column (Waters ®), 3.5 μm, 150 × 4.6 mm, 98/2 Water (0.05% HCOOH)/CH3CN in 10 min 100% CH3CN
**Symmetry C-18 column, Waters, 3.5 μm, 100 × 4.6 mm 98/2 Water (0.05% TFA)/CH3CN in 8 min 100% CH3CN and 5 min at 100%
***Transesterification in the course of reaction.

Example 5: Alkylation of the Monoalkylated Cyclen D, Stereospecific Alkylation

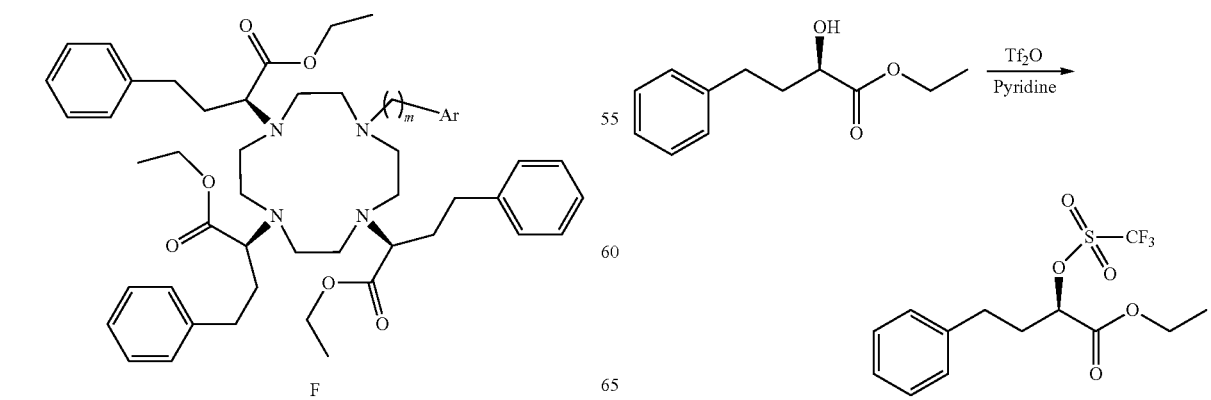

TABLE 6

Alkylating agent E

| Structure of E | Name | Empirical formula, RN, MW (g/mol) |
|---|---|---|
| (structure shown) | Ethyl ester of phenyl-4-butanoic acid of configuration R E4 | $C_{13}H_{15}F_3O_5S$, 88767-98-0 340.32 |

Procedure for Preparing the Triflate Alkylating Agent E4:

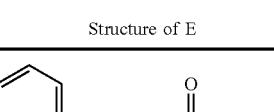

A solution of triflic anhydride in 5 ml of $CH_2Cl_2$ is added dropwise, at 0° C., under argon, to a solution of 15 mmol of ethyl ester of R—(−) hydroxy-2-phenyl-4-butyric acid in 10 ml of $CH_2Cl_2$ and 1.2 ml of pyridine.

The mixture obtained is kept at this same temperature for 1 h, then for 1 h at 15° C., and overnight at room temperature. After filtration to remove the pyridinium salts, the filtrate is concentrated and then chromatographed on $SiO_2$ with an eluent of composition cyclohexane 5/EtOAc 5. The fractions selected and then evaporated give a translucent oil with a yield of 53%, which will quickly be used in the next step. TLC: Rf=0.5 with eluent EtOAc 5/Cyclohexane 5.

Procedure for Alkylation with the Triflate Alkylating Agent E4:

A solution of the triflate reagent E4 prepared beforehand (1.3 mmol in 10 ml of $CH_3CN$) is added dropwise, under argon and at room temperature, to a solution of 3.8 mmol of monofunctionalized cyclen D in 10 ml of $CH_3CN$ and 0.54 ml of diisopropylethylamine. After reaction for 18 h at room temperature, the reaction mixture is filtered and then concentrated before being chromatographed on $SiO_2$ with an eluent of composition $CH_2Cl_2$/MeOH. The fractions are mixed and evaporated, giving an amber-colored oil (yield 41%).

TABLE 7

Alkylation of the monoalkylated cyclen D, Stereospecific alkylation

| Type | Code | Substituent | Yield | Molecular weight (g/mol) | MS (ES+) | HPLC (retention time (tr) |
|---|---|---|---|---|---|---|
| PheEth | F10 | N-(4-phenyl)benzyl | 41% | 909.23 | $C_{57}H_{72}N_4O_6$ 909.7 $[M + H]^+$ 455.38 $[M + 2H]^{2+}$ | tr = 8.52 |

* Sunfire ™ C-18 column (Waters ®), 3.5 μm, 150 × 4.6 mm

Example 6: General Procedure for Saponification of F

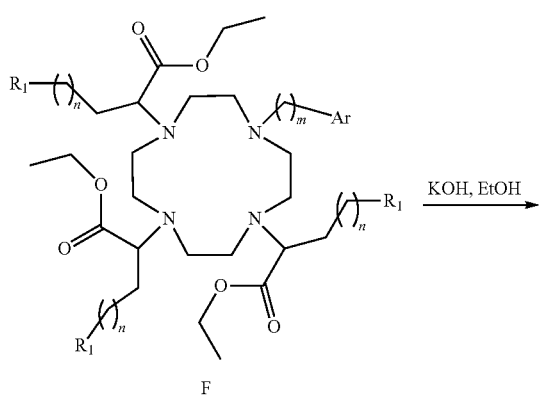

F

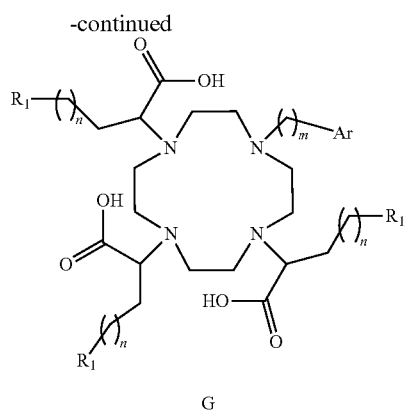

G

The ligand in the form of ethyl ester F (1 eq, 0.5 mmol) is dissolved in ethanol (5 mL), and an alcoholic potash solution (2 mol/L, 10 mL) is added. The reaction mixture is then stirred under reflux for 18 hours. On return to room temperature, the ethanol is evaporated. Addition of hydrochloric acid (1 mol/L) to pH=1 leads to precipitation of a solid. The latter is filtered and washed abundantly with water to remove the salts and give the ligand G.

For the ligand G1, it was possible, at the ester stage, to separate four fractions during purification by silica chromatography. These four fractions were saponified separately to give 4 ligand fractions (G1-Iso1 to G1-Iso4).

TABLE 8

Saponification
Ligands G according to the invention

| Types | Codes | Products | Yields | Molecular weights (g/mol) | MS (ES+) | HPLC (retention time (tr)) |
|---|---|---|---|---|---|---|
| C12 | G1 | -N-(3,5-di-tert-butyl)benzyle | 81% | 969.54 | $C_{59}H_{108}N_4O_6$ 969.8 $[M + H]^+$ | — |
|  | G2 | -N-(4-n-octyl)benzyle | 94% | 969.54 | $C_{59}H_{108}N_4O_6$ 969.8 $[M + H]^+$ | 9.9 min* |
| C10 | G3 | -N-(3,5-di-tert-butyl)benzyle | 19% (purity: 93%) | 884.7 | $C_{53}H_{96}N_4O_6$ 885.72 $[M + H]^+$ | — |

TABLE 8-continued

Saponification
Ligands G according to the invention

| Types | Codes | Products | Yields | Molecular weights (g/mol) | MS (ES+) | HPLC (retention time (tr) |
|---|---|---|---|---|---|---|
| | G4 | -N-[3,5-Bis(trifluomethyl)benzyle] | 30% | 908.6 | $CH_{47}H_{78}F_6N_4O_6$ 909.59 $[M + H]^+$ | — |
| | G5 | -N-[4-(2-PhenylEthyl)-benzyl] | 61% | 877.32 | $C_{53}H_{88}N_4O_6$ 877.73 $[M + H]^+$ | 7.8 min* |

TABLE 8-continued
Saponification
Ligands G according to the invention
| Types | Codes | Products | Yields | Molecular weights (g/mol) | MS (ES+) | HPLC (retention time (tr) |
|---|---|---|---|---|---|---|
| | G6 | -N-(4-phenyl)benzyle | 90% | 849.26 | $C_{51}H_{84}N_4O_6$ 849.72 $[M + H]^+$ | 7.5 min* |
| | G7 | -N-(4-n-octyl)benzyle | 86% | 885.38 | $C_{53}H_{96}N_4O_6$ 885.7 $[M + H]^+$ | 8.4 min* |
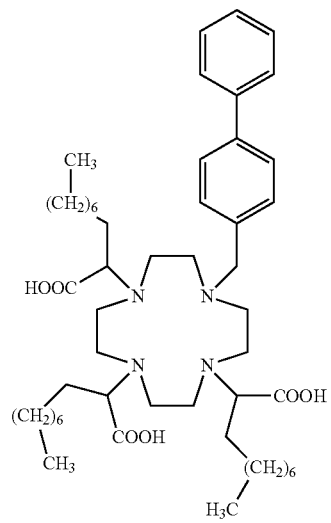
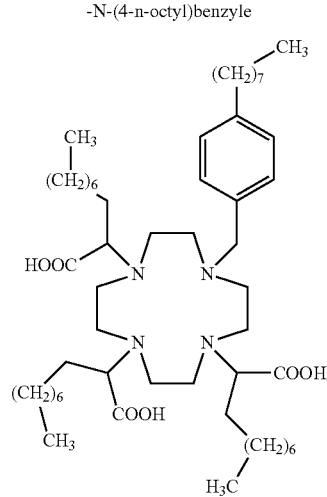

TABLE 8-continued

Saponification
Ligands G according to the invention

| Types | Codes | Products | Yields | Molecular weights (g/mol) | MS (ES+) | HPLC (retention time (tr) |
|---|---|---|---|---|---|---|
| C8 | G8 | -N-(4-n-octyl)benzyle | 25% | 801.6 | $C_{47}H_{84}N_4O_6$ 801.6 $[M + H]^+$ | — |
|  | G9 | -N-[4-(2-PhenylEthyl)-benzyl] | 70% | 793.2 | $C_{47}H_{76}N_4O_6$ 793.59 $[M + H]^+$ | 6.4 min* |

TABLE 8-continued

Saponification
Ligands G according to the invention

| Types | Codes | Products | Yields | Molecular weights (g/mol) | MS (ES+) | HPLC (retention time (tr) |
|---|---|---|---|---|---|---|
| PheEth. | G10 | -N-(4-phenyl)benzyle | 20% | 825.07 | 826 [M + H]+ 413 [M + 2H]$^{2+}$ | 8.08 min* |
| C10 | G11 | N-(2-(4'-pentyl-[1,1'-biphenyl]-4-yl)ethyl) | 90% | 933.42 | C57H96N4O6 [M + H]+ 933.8 | 9.8 min 10.0 min** |

TABLE 8-continued

Saponification
Ligands G according to the invention

| Types | Codes | Products | Yields | Molecular weights (g/mol) | MS (ES+) | HPLC (retention time (tr) |
|---|---|---|---|---|---|---|
| | G12 | -(2-(4'-octyl-[1,1'-biphenyl]-4-yl)ethyl) | 33% | 975.50 | C60H102N4O6 [M + H]+ 975.8 | 10.3 min** |

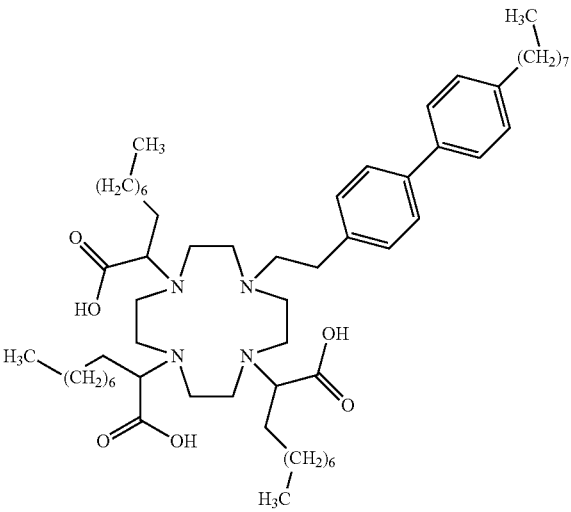

*Sunfire ™ C-18 column (Waters ®), 3.5 μm, 150 × 4.6 mm, 98/2 Water (0.05% HCOOH)/CH3CN in 10 min 100% CH3CN

**Symmetry C-18 column, Waters, 3.5 μm, 100 × 4.6 mm 98/2 Water (0.05% HCOOH)/CH3CN in 12 min 100% CH3CN and 8 min at 100%*

III. Synthesis of the Complexes:

Example 7: General Procedure for Complexation of G with Yttrium 89

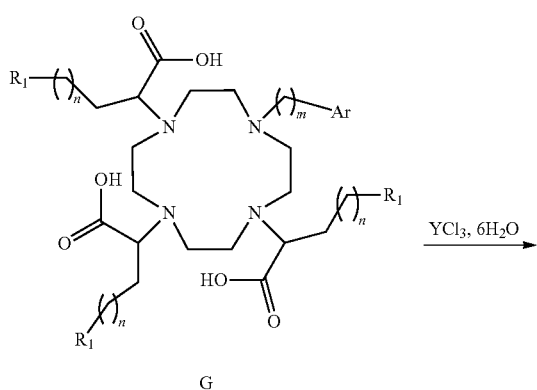

G $\xrightarrow{YCl_3, 6H_2O}$

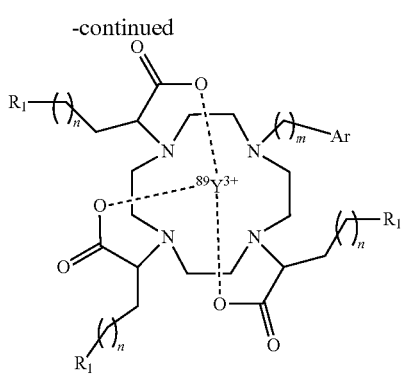

H

The ligand G (1 eq, 0.07 mmol) is dissolved in 3 mL of methanol (pH=6). Yttrium chloride hexahydrate (1.5 eq, 0.1 mmol) is then added (pH=4). This is followed by controlled addition of a solution of sodium methoxide to obtain neutral pH. The mixture is stirred and heated at 65° C. overnight. At the end of the reaction, the solvent is evaporated and the solid obtained is washed abundantly with water to give the complex H.

TABLE 9

Complexation of G with yttrium 89
Complexes of yttrium 89 H

| Types | Codes | Products | Yields | Molecular weights (g/mol) | MS (ES+) |
|---|---|---|---|---|---|
| C12 | H2 | -N-(4-n-octyl)benzyle | 70% | 1055.42 | $C_{59}H_{105}N_4O_6Y$ 1055.7 $[M + H]^+$ |
| C10 | H3 | -N-(3,5-di-tert-butyl)benzyle | 85% | 971.3 | $C_{53}H_{93}N_4O_6Y$ 971.6 $[M + H]^+$ |
|  | H4 | -N-[3,5-Bis(trifluométhyl)benzyle | 80% | 994.5 | $C_{47}H_{75}F_6N_4O_6Y$ 995.46 $[M + H]^+$ |
|  | H5 | -N-[4-(2-PhenylEthyl)-benzyl | — | 963.20 | $C_{53}H85N4O6Y$ 963.6 $[M + H]^+$ |
|  | H7 | -N-(4-n-octyl)benzyle | 82% | 971.26 | $C_{53}H_{93}N_4O_6Y$ 971.6 $[M + H]^+$ |
| C8 | H8 | -N-(4-n-octyl)benzyle | 93% | 887.1 | $C_{47}H_{81}N_4O_6Y$ 887.5 $[M + H]^+$ |
|  | H9 | -N-[4-(2-PhenylEthyl)-benzyl | 64% | 879.0 | $C_{47}H_{73}N_4O_6Y$ 879.42 $[M + H]^+$ |

Symmetry Sunfire ™ C-18 column, 3.5 μm, 150 × 4.6 mm

IV. Radiochemistry:

The following equipment was used for radiolabeling (Table 9):

| Bottles | 12 mL, borosilicate glass, crimped Elu-lll | IBA |
|---|---|---|
| Incubator | Fisherbrand 15 L | Fisher |
| Tubes | 5 mL made of PP with screwed stopper white | VWR |
| Syringes | 1 mL BD Plastipak ® | Becton-Dickinson |
| Needles | BD Microlance 21G 2" | Becton-Dickinson |
| Activity meter | CRC-127R | Capintec |
| Counter | Cobra II Auto-gamma | Packard |

The experiments were carried out in crimped borosilicate glass bottles. The bottles were heated in a Bioblock heating block suitable for heating up to 6 bottles. When stirring was necessary, a Lab Dancer S40 vortex (VWR) was used. The centrifugations were carried out with an MF 20-R centrifuge (Awel).

The activities were measured in a CRC-127R activity meter (Capintec), which was calibrated each morning.

Quality controls were performed by TLC on Whatman 1 paper, with MeOH/NEt$_3$ 0.1% mixture as eluent. The Radio-Chemical Purity (RCP) is determined using a Cyclone phosphoimager (Perkin Elmer), and processed with Optiquant software.

Example 8: General Procedure for Complexation of G with Yttrium 90

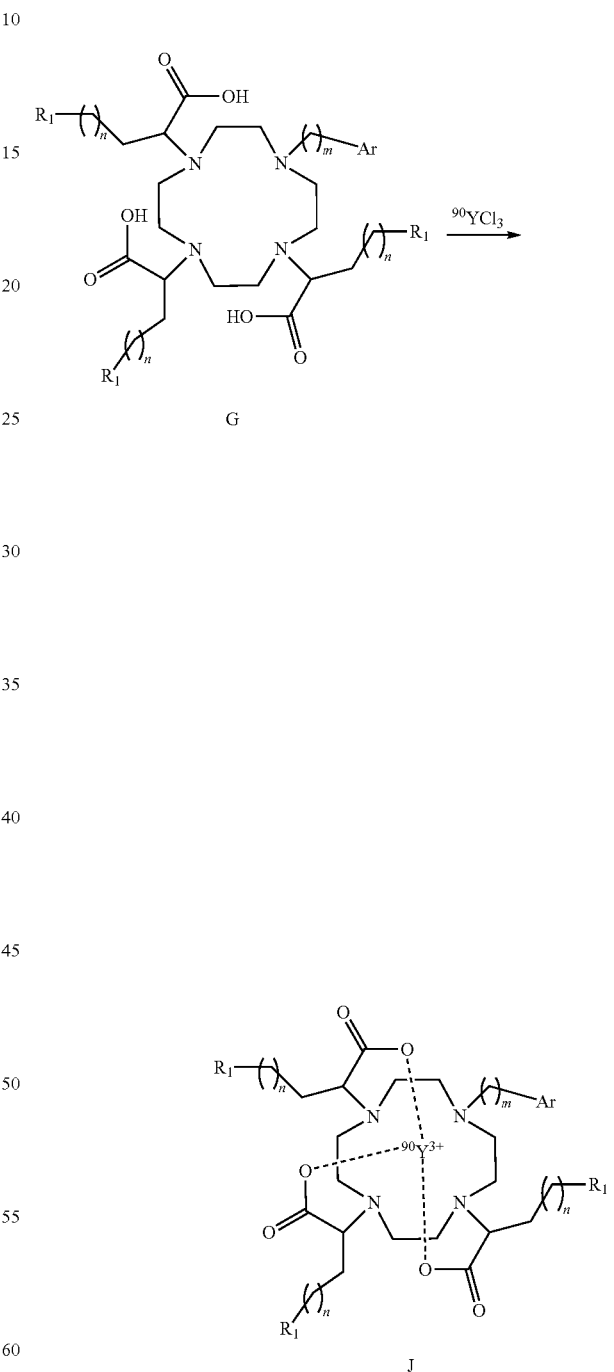

1 mL of yttrium-90 chloride in solution in an acetate buffer pH=7 is added to 1 mL of ligand G in solution in ethanol at a concentration of $10^{-3}$ mol/L. The solution is heated at 90° C. for 30 min. The yttrium 90 complex J is thus obtained.

TABLE 11

Radiolabeling yield
Radiolabeling yield, %

| | Ligands | | | | | | | | | | | | | | |
|---|---|---|---|---|---|---|---|---|---|---|---|---|---|---|---|
| | G1iso1 | G1iso2 | G1iso3 | G1iso4 | G2 | G3 | G4 | G5 | G6 | G7 | G8 | G9 | G10 | G11 | G12 |
| Complexes $^{90}$Y J | 89 | 94.4 | 81.5 | 95.5 | 14.1 | 97.4 | 96 | 98.7 | 97.9 | 36.3 | 78.8 | 82.3 | 90 | 76.5 | 35.7 |

The results are also presented in FIG. 1.

It can be seen that the ligands according to the invention have a radiolabeling yield that is satisfactory, or even very good, and notably greater than 75%.

Example 9: General Procedure for Extraction in Iodinated Poppyseed Oil 2 mL of Lipiodol® is added to the complex J prepared in example 8 and the mixture is stirred vigorously. The phases are then separated by centrifugation (3500 rev/min, 15 min) and the oily phase is collected to give the expected radioactive tracer H. The activity of the oily phase H is then measured to evaluate the degree of extraction of the radiolabeled complex J.

TABLE 12

Extraction yield of the radiolabeled complex J %
Extraction yield of the radiolabeled complex J, %

| | Complexes $^{90}$Y J | | | | | | | | | | | | | | |
|---|---|---|---|---|---|---|---|---|---|---|---|---|---|---|---|
| | J1iso1 | J1iso2 | J1iso3 | J1iso4 | J2 | J3 | J4 | J5 | J6 | J7 | J8 | J9 | J10 | J11 | J12 |
| Radioactive tracer $^{90}$Y H | 96.8 | 99.2 | 41.1 | 75.7 | 41.8 | 96.7 | 99.0 | 97.7 | 96.9 | 64.3 | 87.4 | 88.4 | 76.2 | 75.9 | 52.2 |

Figure 2:
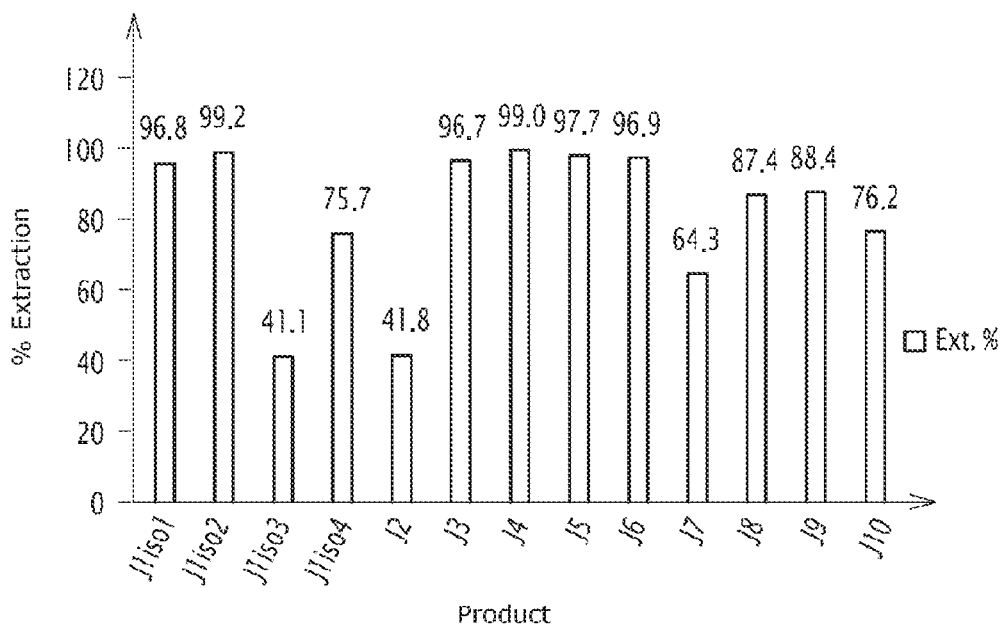
FIG. 2 shows the degree of extraction in the oily phase as a percentage for complexes according to the invention.

The results are also presented in FIG. 2.

It can be seen that the extraction yields of the complexes according to the invention in Lipiodol® are satisfactory, or even above 75%: they are therefore easily extractable in an oily phase.

Example 10: General Procedure for Evaluating the Stability of the Radioactive Tracer H Assay of the yttrium-90 salted-out in the aqueous solution (normal saline solution or human serum) over time is carried out by counting with the gamma counter. The latter is calibrated beforehand for measuring yttrium-90 (calculation of the counting yield of the apparatus for this isotope).

At different time points, an aliquot of 100 µL is taken from each sample and deposited in a previously weighed 5-mL tube. The tubes are weighed and then counted with the gamma counter. The measurements obtained are corrected for the counting yield and the decrease of yttrium-90 to determine the percentage of yttrium-90 salted-out in the aqueous phase, relative to the initial activity present in the solution. The weight of liquid taken was also taken into account.

1 mL of freshly prepared radioactive tracer H is taken and then deposited in a 12-mL flat-bottomed glass bottle. The activity is measured with the activity meter, and the time is noted. 10 mL of 0.9% saline solution (normal saline solution) is added and the mixture is stirred. The bottle is then put in the incubator set at 37° C., equipped with a stirrer set at 30 rpm.

It is stirred for several days. Samples are taken from the aqueous phase at different times for assay of the yttrium-90 salted-out.

TABLE 13

Stability at 7 or 8 days in normal saline solution 7 d stability test. Normal saline solution

| | Radioactive tracer | | | | | | | | | |
|---|---|---|---|---|---|---|---|---|---|---|
| | H1iso1 | H1iso2 | H1iso3 | H1iso4 | H3 | H5 | H6 | H7 | H8 | H9 | H10 |
| % 7 d | 6.8 | 4.15 | 14.7 | 15.7 | 9.8 | 3 | 0.5 | 4.4 | 2.4 | 9.5 | 9 |

| | Radioactive tracer | |
|---|---|---|
| | H11 | H12 |
| % 8 d | 19.7 | 8.6 |

Figure 3:
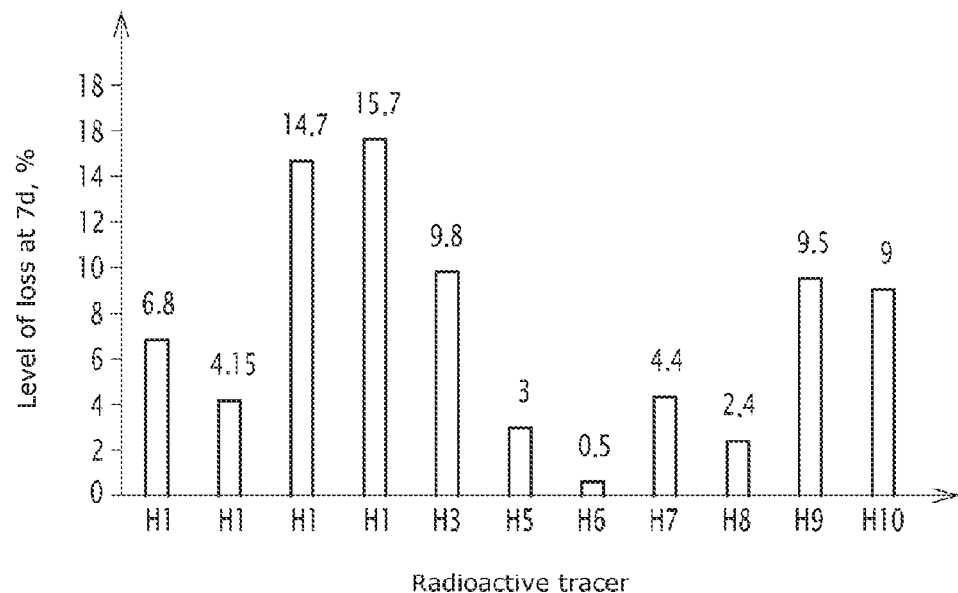
FIG. 3 shows the stability test in normal saline solution, giving the percentage level of loss as a function of radioactive tracers according to the invention.

The results are also presented in FIG. 3.

Example 11: Stability Test in Normal Saline Solution at 15 Days 1 mL of freshly prepared radioactive tracer H is taken and then deposited in a 12-mL flat-bottomed glass bottle. The activity is measured with the activity meter, and the time is noted. 10 mL of 0.9% saline solution (normal saline solution) is added and the mixture is stirred. The bottle is then put in the incubator set at 37° C., equipped with a stirrer set at 30 rpm.
It is stirred for 15 days. Samples of the aqueous phase are taken at different times for assay of the yttrium-90 salted-out.

Figure 4:
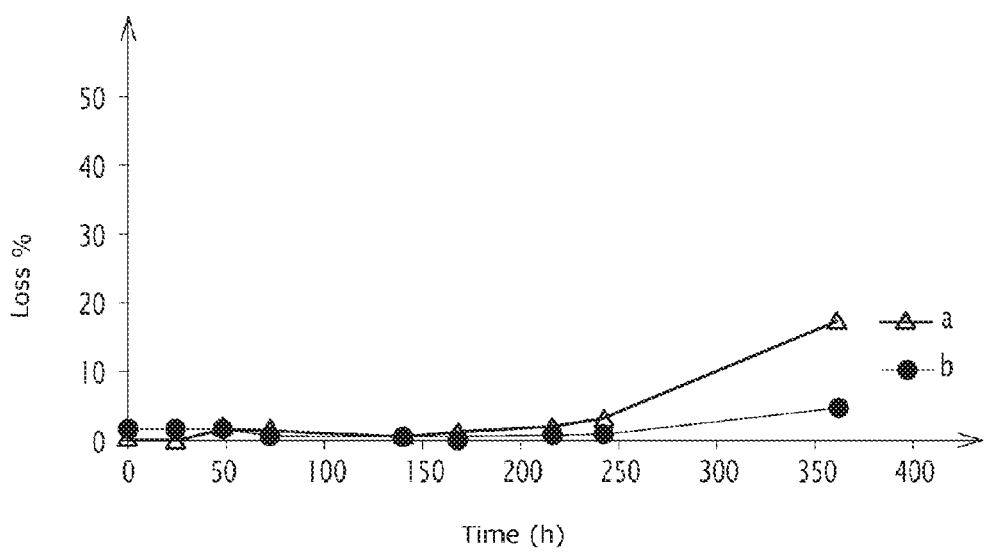
FIG. 4 shows the percentage level of loss in normal saline solution of the radioactive tracers H5 (a) and H6 (b) according to the invention.

The results are presented in Table 14 below as well as in FIG. 4.

TABLE 14

Stability at 15 d in normal saline solution

| [Time (h)] | H5 % | H6 % |
|---|---|---|
| 1 | 0.5 | 1.56 |
| 24 | 0.27 | 1.52 |
| 48 | 1.5 | 1.23 |
| 72 | 1.06 | 0.57 |
| 138 | 0.71 | 0.71 |
| 168 | 1.07 | 0.61 |
| 216 | 2.03 | 0.74 |
| 240 | 3.32 | 0.96 |
| 360 | 17.67 | 4.9 |

Example 12: Stability Test in Human Serum at 15 Days 1 mL of freshly prepared radioactive tracer H is taken and then deposited in a 12-mL flat-bottomed glass bottle. The activity is measured with the activity meter, and the time is noted. 10 mL of human serum is added and the mixture is stirred. The bottle is then put in the incubator set at 37° C., equipped with a stirrer set at 30 rpm. It is stirred for 15 days. Samples of the aqueous phase are taken at different times for assay of the yttrium-90 salted-out.

Figure 5:
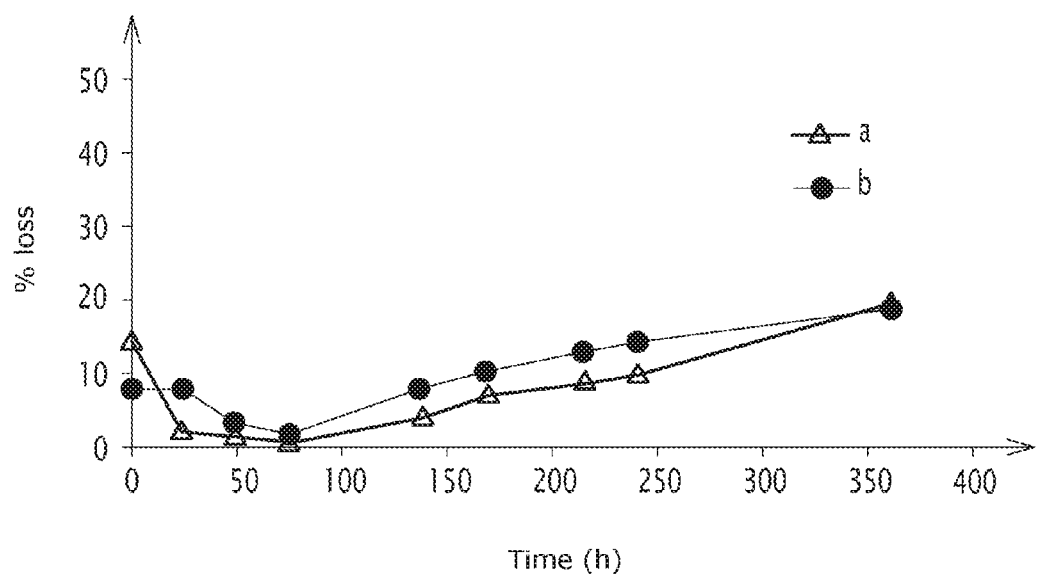
FIG. 5 shows the percentage level of loss in normal saline solution of the radioactive tracers H5 (a) and H6 (b) according to the invention.

The results are presented in Table 15 below as well as in FIG. 5.

TABLE 15

Stability at 15 d in human serum

| [Time (h)] | H5 % | H6 % |
|---|---|---|
| 1 | 14.18 | 7.73 |
| 24 | 2.4 | 7.7 |
| 48 | 1.41 | 3.17 |
| 72 | 1 | 2.1 |
| 138 | 4.18 | 7.98 |
| 168 | 6.69 | 10.15 |
| 216 | 8.83 | 12.95 |
| 240 | 9.64 | 14.26 |
| 360 | 19.44 | 18.5 |

It can be concluded from the stability tests that the complexes according to the invention are stable in an oily phase and are not lost into an aqueous phase such as normal saline solution. This stability notably allows excellent vectoring of the complexes when administered to patients in an oily phase such as Lipiodol®.

The invention claimed is:
1. A compound of formula (I):

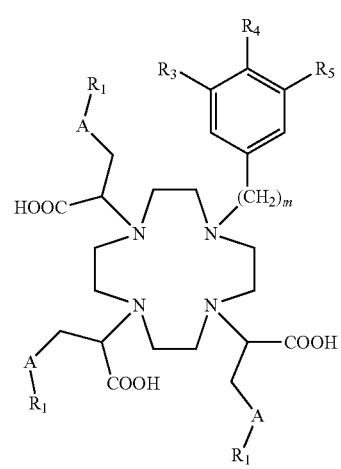

wherein:
$R_1$ is a methyl or a $(C_6-C_{10})$aryl;
$R_3$, $R_4$ and $R_5$ are selected independently of one another from the group consisting of: H, $(C_1-C_{20})$alkyl, $(C_2-C_{20})$alkenyl, $(C_2-C_{20})$alkynyl, $(C_6-C_{10})$aryl, $(C_1-C_{20})$alkylene-$(C_6-C_{10})$aryl, $(C_2-C_{20})$alkenylene-$(C_6-C_{10})$aryl and $(C_2-C_{20})$alkynylene-$(C_6-C_{10})$aryl;

said alkyl, alkenyl, alkynyl, alkylene, alkenylene and alkynylene groups of the radicals $R_3$, $R_4$ and $R_5$ may optionally comprise one or more ($C_6$-$C_{10}$)arylene(s) and/or one or more ($C_5$-$C_{10}$)cycloalkylene(s) in their chain; and said alkyl, alkenyl, alkynyl, aryl, alkylene, alkenylene and alkynylene groups of the radicals $R_3$, $R_4$ and $R_5$ optionally being substituted with one or more substituent(s) selected from the group consisting of: halogen, halo($C_1$-$C_{20}$)alkyl, ($C_1$-$C_{20}$)alkyl, ($C_2$-$C_{20}$)alkenyl, ($C_2$-$C_{20}$)alkynyl; said alkyl, alkenyl and alkynyl groups optionally comprising one or more ($C_6$-$C_{10}$)arylene(s) in their chain;

A is a group —$(CH_2)_n$— which may optionally comprise one or more ($C_6$-$C_{10}$)arylene(s) in its chain;

n is an integer in the range from 0 to 15; and m is an integer in the range from 1 to 10;

or a pharmaceutically acceptable salt thereof or an optical isomer thereof or a geometric isomer thereof or a tautomer thereof or a solvate thereof.

2. The compound of formula (I) as claimed in claim 1, in which when $R_1$ is a methyl, n is an integer in the range from 4 to 8.

3. The compound as claimed in claim 1, of formula (I-1):

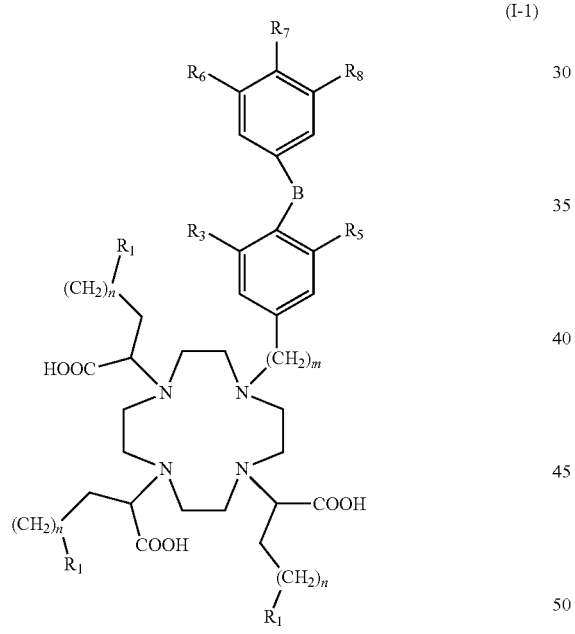

wherein:

$R_1$ is a methyl or a ($C_6$-$C_{10}$)aryl;

$R_3$ and $R_5$ are selected independently of one another from the group consisting of: H, ($C_1$-$C_{20}$)alkyl, ($C_2$-$C_{20}$)alkenyl, ($C_2$-$C_{20}$)alkynyl, ($C_6$-$C_{10}$)aryl, ($C_1$-$C_{20}$)alkylene-($C_6$-$C_{10}$)aryl, ($C_2$-$C_{20}$)alkenylene-($C_6$-$C_{10}$)aryl and ($C_2$-$C_{20}$)alkynylene-($C_6$-$C_{10}$)aryl;

said alkyl, alkenyl, alkynyl, alkylene, alkenylene and alkynylene groups of the radicals $R_3$, $R_4$ and $R_5$ may optionally comprise one or more ($C_6$-$C_{10}$)arylene(s) and/or one or more ($C_5$-$C_{10}$)cycloalkylene(s) in their chain; and said alkyl, alkenyl, alkynyl, aryl, alkylene, alkenylene and alkynylene groups of the radicals $R_3$, $R_4$ and $R_5$ optionally being substituted with one or more substituent(s) selected from the group consisting of: halogen, halo($C_1$-$C_{20}$)alkyl, ($C_1$-$C_{20}$)alkyl, ($C_2$-$C_{20}$)alkenyl, ($C_2$-$C_{20}$)alkynyl; said alkyl, alkenyl and alkynyl groups optionally comprising one or more ($C_6$-$C_{10}$)arylene(s) in their chain;

n is an integer in the range from 0 to 15;

m is an integer in the range from 1 to 10;

B is a bond, a ($C_1$-$C_{20}$)alkylene, a ($C_2$-$C_{20}$)alkenylene or a ($C_2$-$C_{20}$)alkynylene; and $R_6$, $R_7$ and $R_8$ are selected, independently of one another, from H and ($C_1$-$C_{20}$)alkyl.

4. The compound as claimed in claim 1, of formula (I-2) or (I-3):

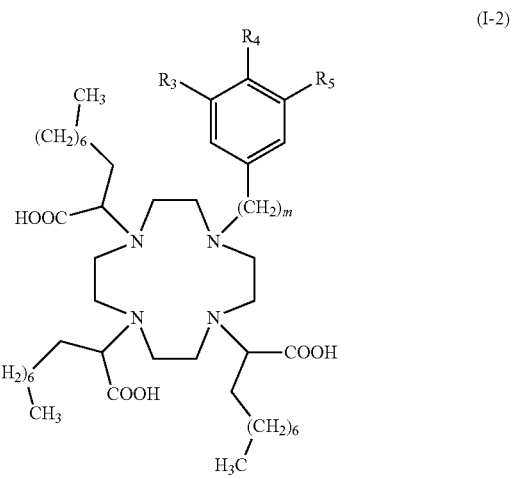

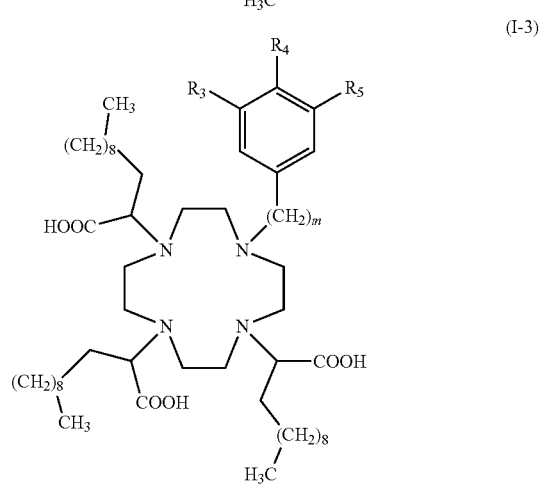

wherein:

$R_3$, $R_4$ and $R_5$ are selected independently of one another from the group consisting of: H, ($C_1$-$C_{20}$)alkyl, ($C_2$-$C_{20}$)alkenyl, ($C_2$-$C_{20}$)alkynyl, ($C_6$-$C_{10}$)aryl, ($C_1$-$C_{20}$)alkylene-($C_6$-$C_{10}$)aryl, ($C_2$-$C_{20}$)alkenylene-($C_6$-$C_{10}$)aryl and ($C_2$-$C_{20}$)alkynylene-($C_6$-$C_{10}$)aryl;

said alkyl, alkenyl, alkynyl, alkylene, alkenylene and alkynylene groups of the radicals $R_3$, $R_4$ and $R_5$ may optionally comprise one or more ($C_6$-$C_{10}$)arylene(s) and/or one or more ($C_5$-$C_{10}$)cycloalkylene(s) in their chain; and said alkyl, alkenyl, alkynyl, aryl, alkylene, alkenylene and alkynylene groups of the radicals $R_3$, $R_4$ and $R_5$ optionally being substituted with one or more substituent(s)

selected from the group consisting of: halogen, halo(C$_1$-C$_{20}$)alkyl, (C$_1$-C$_{20}$)alkyl, (C$_2$-C$_{20}$)alkenyl, (C$_2$-C$_{20}$)alkynyl; said alkyl, alkenyl and alkynyl groups optionally comprising one or more (C$_6$-C$_{10}$)arylene(s) in their chain; and m is an integer in the range from 1 to 10.

5. The compound of formula (I) as claimed in claim 1, selected from the group consisting of the following compounds:

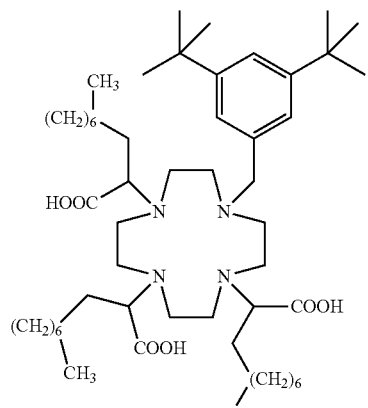
G3

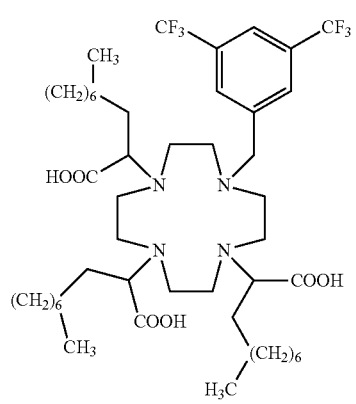
G4

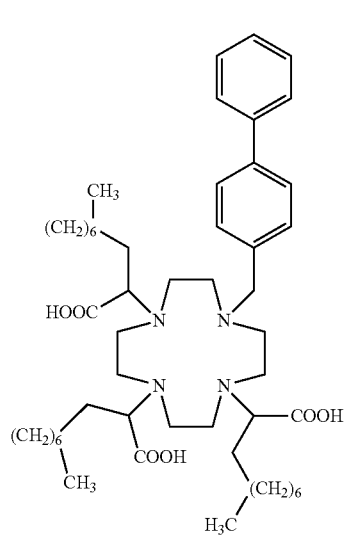
G6

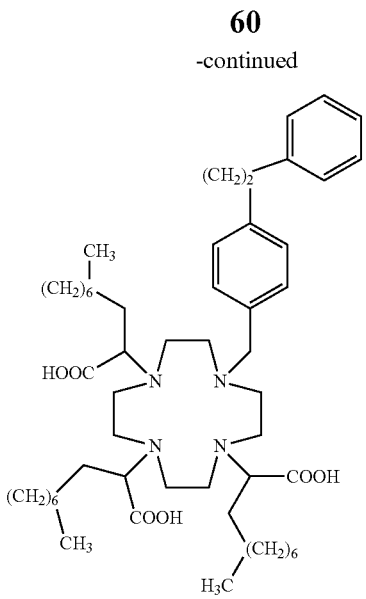
G5

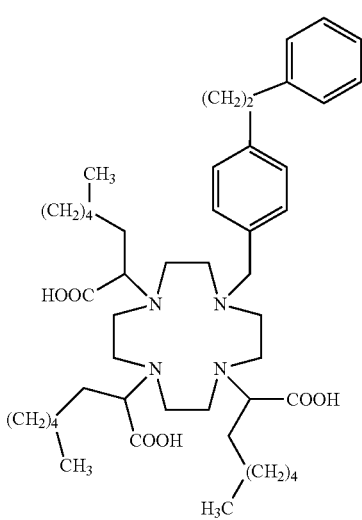
G9

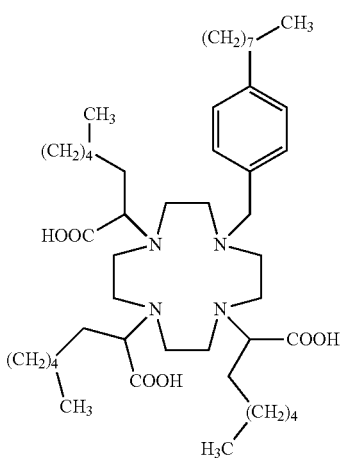
G8

-continued
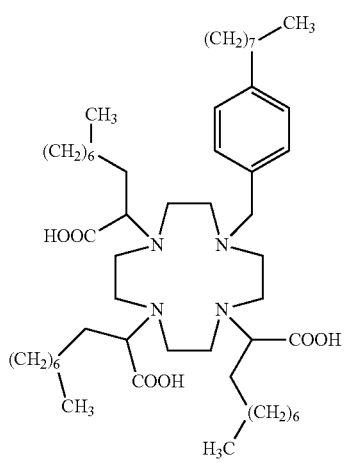
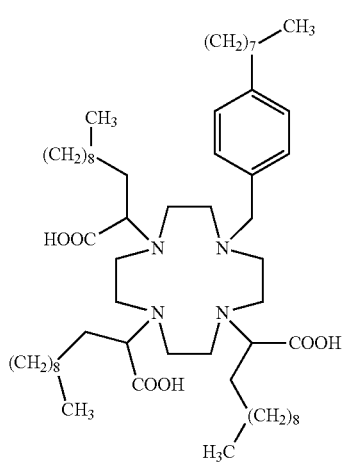
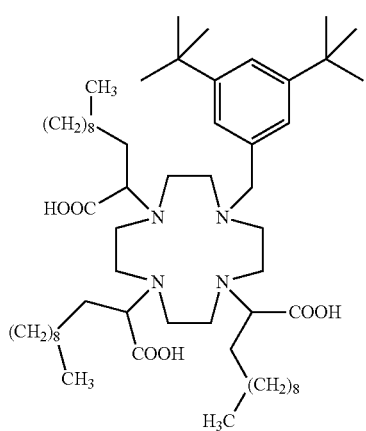
-continued
G7
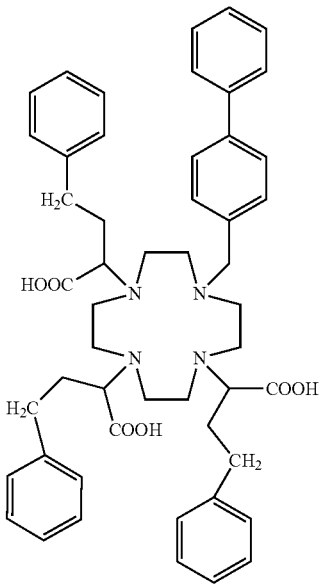
G10
G2
G11
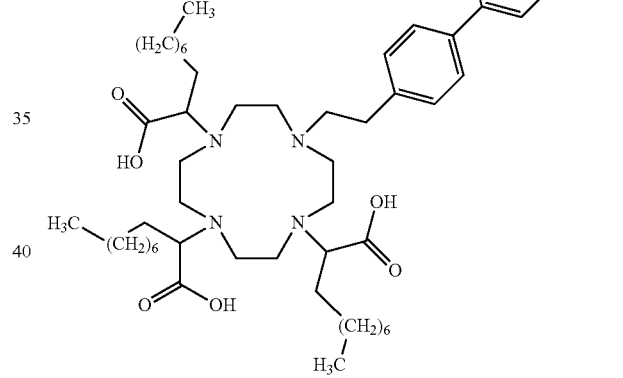
G1
G12
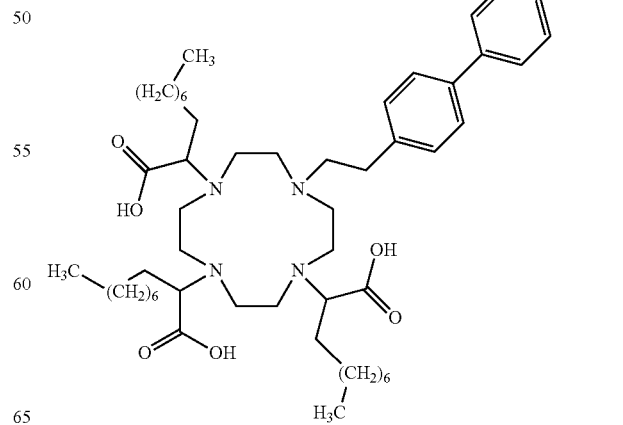
or their pharmaceutically acceptable salts.

6. A complex of a compound of formula (I) or of a salt thereof as claimed in claim 1, with M; M being a chemical element.

7. A method for treating cancer comprising administering to a mammal in need thereof a therapeutically effective amount of the complex as claimed in claim 6.

8. A pharmaceutical composition comprising the compound as claimed in claim 1 and optionally one or more pharmaceutically acceptable excipients.

9. The pharmaceutical composition as claimed in claim 8, further comprising an iodinated oil.

10. The compound as claimed in claim 3, wherein n is equal to 6 or is equal to 8.

11. The complex as claimed in claim 6, wherein M is a radioelement.

12. The method for treating cancer as claimed in claim 7, wherein the cancer is liver cancer.

13. The pharmaceutical composition as claimed in claim 9, wherein the iodinated oil is an iodinated oil comprising iodinated ethyl esters of fatty acids of poppyseed oil.

14. A pharmaceutical composition comprising the complex as claimed in claim 6 and optionally one or more pharmaceutically acceptable excipients.

15. The pharmaceutical composition as claimed in claim 14, further comprising an iodinated oil.

16. The pharmaceutical composition as claimed in claim 15, wherein the iodinated oil is an iodinated oil comprising iodinated ethyl esters of fatty acids of poppyseed oil.

\* \* \* \* \*